US012721906B2

(12) United States Patent
Abdi

(10) Patent No.: US 12,721,906 B2
(45) Date of Patent: Sep. 1, 2026

(54) KIDNEY TARGETED DELIVERY OF DRUGS

(71) Applicant: The Brigham and Women's Hospital, Inc., Boston, MA (US)

(72) Inventor: Reza Abdi, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 684 days.

(21) Appl. No.: 18/030,689

(22) PCT Filed: Oct. 8, 2021

(86) PCT No.: PCT/US2021/054204
§ 371 (c)(1),
(2) Date: Apr. 6, 2023

(87) PCT Pub. No.: WO2022/076840
PCT Pub. Date: Apr. 14, 2022

(65) Prior Publication Data

US 2023/0364259 A1 Nov. 16, 2023

Related U.S. Application Data

(60) Provisional application No. 63/089,126, filed on Oct. 8, 2020.

(51) Int. Cl.
*A61K 47/68* (2017.01)
*A61K 47/69* (2017.01)

(52) U.S. Cl.
CPC ...... *A61K 47/6891* (2017.08); *A61K 47/6937* (2017.08)

(58) Field of Classification Search
None
See application file for complete search history.

(56) References Cited

FOREIGN PATENT DOCUMENTS

| | | | |
|---|---|---|---|
| WO | WO-2015184099 A1 * | 12/2015 | ............. A61P 37/02 |
| WO | WO 2016/153920 | 9/2016 | |
| WO | WO-2016153920 A1 * | 9/2016 | ........... A61K 31/192 |
| WO | WO-2017026502 A1 * | 2/2017 | ............. C12N 15/09 |

OTHER PUBLICATIONS

Zhou et al., Acta Pharm Sin B. Jan. 23, 2014;4(1):37-42 (Year: 2014).*

Wang et al., Biomater Sci. Jul. 25, 2017;5(8):1450-1459 (Year: 2017).*

Klassen et al., J Appl Physiol (1985) Jan. 2005;98(1):257-63 (Year: 1985).*

Translation, WO 2017026502 downloaded Nov. 25, 2025 from https://patents.google.com/patent/WO2017026502A1/en?oq=2017026502. (Year: 2017).*

(Continued)

*Primary Examiner* — Karl J Puttlitz
(74) *Attorney, Agent, or Firm* — Fish & Richardson P.C.

(57) ABSTRACT

The present disclosure provides, inter alia, compositions comprising drug-containing polymeric particles, wherein each drug-containing polymeric particle is attached to one or more immunoglobulin light chains or a megalin-binding fragment thereof. Methods of preparing and using these drug-containing polymeric particles are also provided.

20 Claims, 14 Drawing Sheets

Specification includes a Sequence Listing.

(56) References Cited

OTHER PUBLICATIONS

Ordikhania et al., Nano Today, vol. 35, Dec. 2020, 100990 (Year: 2020).*
Abshire et al., "Focused Ultrasound-Triggered Release of Tyrosine Kinase Inhibitor from Thermosensitive Liposomes for Treatment of Renal Cell Carcinoma," Journal of Pharmaceutical Sciences, May 2017, 106(5):1355, 23 pages.
Adamy et al., "Clinical characteristics and outcomes of patients with recurrence 5 years after nephrectomy for localized renal cell carcinoma," The Journal of Urology, Feb. 2011, 185(2):433-8.
Akita et al., "A neutral lipid envelope-type nanoparticle composed of a pH-activated and vitamin E-scaffold lipid-like material as a platform for a gene carrier targeting renal cell carcinoma," Journal of Controlled Release, Feb. 2015, 200:97, 26 pages.
Alsaab et al., "Tumor hypoxia directed multimodal nanotherapy for overcoming drug resistance in renal cell carcinoma and reprogramming macrophages," Biomaterials, Nov. 2018, 183:280, 30 pages.
Andres et al., "Histology of human tubulo-interstitial nephritis associated with antibodies to renal basement membranes," Kidney International, Jun. 1978, 13(6):480-91.
Artinger et al., "Innate and adaptive immunity in experimental glomerulonephritis: a pathfinder tale, " Pediatric Nephrology, Jun. 2017, 32:943-7.
Asgeirsdottir et al., Site-specific inhibition of glomerulonephritis progression by targeted delivery of dexamethasone to glomerular endothelium, Molecular Pharmacology, Jul. 2007, 72(1):121-31.
Atkins, R.C., et al., Modulators of crescentic glomerulonephritis. J Am Soc Nephrol, 1996. 7(11): p. 2271-8.
Bariéty et al., "Podocyte involvement in human immune crescentic glomerulonephritis," Kidney International, Sep. 2005, 68(3):1109-19.
Basnayake et al., "The biology of immunoglobulin free light chains and kidney injury," Kidney International, Jun. 2011, 79(12):1289-301.
Bennett et al., "MRI of the basement membrane using charged nanoparticles as contrast agents," Magnetic Resonance in Medicine, Sep. 2008, 60(3):564-74.
Callaghan et al., "Combined treatment of tyrosine kinase inhibitor-labeled gold nanorod encapsulated albumin with laser thermal ablation in a renal cell carcinoma model," Journal of Pharmaceutical Sciences, Jan. 2016, 105(1):284-92.
Chai et al., "Combining DNA vaccine and AIM2 in H1 nanoparticles exert anti-renal carcinoma effects via enhancing tumor-specific multi-functional CD8+ T-cell responses," Molecular Cancer Therapeutics, Feb. 2019, 18(2):323-34.
Chai et al., "H1/pAIM2 nanoparticles exert anti-tumour effects that is associated with the inflammasome activation in renal carcinoma," Journal of Cellular and Molecular Medicine, Nov. 2018, 22(11);5670-81.
Choi et al., "Targeting kidney mesangium by nanoparticles of defined size," Proceedings of the National Academy of Sciences, Apr. 2011, 108(16):6656-61.
Conner et al., "Evaluation of near infrared fluorescent labeling of monoclonal antibodies as a tool for tissue distribution," Drug Metabolism and Disposition, Nov. 2014, 42(11):1906, 30 pages.
Cunningham et al., "Prominence of cell-mediated immunity effectors in "pauci immune" glomerulonephritis," Journal of the American Society of Nephrology, Mar. 1999, 10(3):499-506.
Dolman et al., "Drug targeting to the Kidney: Advances in the active targeting of therapeutics to proximal tubular cells," Advanced Drug Delivery Reviews, Nov. 2010, 62(14):1344-57.
Donat et al., "Follow-up for clinically localized renal neoplasms: AUA guideline," The Journal of Urology, Aug. 2013, 190(2):407-16.
Eggener et al., "Renal cell carcinoma recurrence after nephrectomy for localized disease: predicting survival from time of recurrence," Journal of Clinical Oncology, Jul. 2006, 24(19):3101-6.
Eshbach et al., "Receptor-mediated endocytosis in the proximal tubule," Annual Review of Physiology, Feb. 2017, 79:425, 27 pages.
Farokhzad et al., "Impact of nanotechnology on drug delivery," ACS Nano, Jan. 2009, 3(1):16-20.
Farokhzad, "Nanotechnology for drug delivery: the perfect partnership," Expert Opinion on Drug Delivery, Sep. 2008, 5(9):927-9.
Ferrari, "Cancer nanotechnology: opportunities and challenges," Nature Reviews Cancer, Mar. 2005, 5(3):161-71.
Filippone et al., "The nephrotoxicity of vancomycin," Clinical Pharmacology & Therapeutics, Sep. 2017, 102(3):459-69.
Gao et al., "Megalin-mediated specific uptake of chitosan/siRNA nanoparticles in mouse kidney proximal tubule epithelial cells enables AQP1 gene silencing," Theranostics, 2014, 4(10):1039-51.
Gentile et al., "An overview of poly (lactic-co-glycolic) acid (PLGA)-based biomaterials for bone tissue engineering," International Journal of Molecular Sciences, Feb. 2014, 15(3):3640-59.
Gustafson et al., "Nanoparticle uptake: the phagocyte problem," Nano Today, Aug. 2015, 10(4):487, 36 pages.
Hafez et al., "Patterns of tumor recurrence and guidelines for followup after nephron sparing surgery for sporadic renal cell carcinoma," The Journal of Urology, Jun. 1997, 157(6):2067-70.
Hori et al., "Megalin blockade with cilastatin suppresses drug-induced nephrotoxicity," Journal of the American Society of Nephrology: JASN, Jun. 2017, 28(6):1783-91.
Hutchison et al., "The pathogenesis and diagnosis of acute kidney injury in multiple myeloma," Nature Reviews Nephrology, Jan. 2012, 8(1):43-51.
Janzen et al., "Surveillance after radical or partial nephrectomy for localized renal cell carcinoma and management of recurrent disease," Urologic Clinics, Nov. 2003, 30(4):843-52.
Jayne et al., "A randomized trial of maintenance therapy for vasculitis associated with antineutrophil cytoplasmic autoantibodies," New England Journal of Medicine, Jul. 2003, 349(1):36-44.
Jennette, "Rapidly progressive crescentic glomerulonephritis, " Kidney International, Mar. 2003, 63(3):1164-77.
Kamaly et al., "Nanomedicines for renal disease: current status and future applications," Nature Reviews Nephrology, Dec. 2016, 12(12):738, 40 pages.
Kamaly et al., "Targeted polymeric therapeutic nanoparticles: design, development and clinical translation," Chemical Society Reviews, 2012, 41(7):2971, 75 pages.
Keefe et al., "Efficacy of the nanoparticle-drug conjugate CRLX101 in combination with bevacizumab in metastatic renal cell carcinoma: results of an investigator-initiated phase I-IIa clinical trial," Annals of Oncology, Aug. 2016, 27(8):1579-85.
Kim et al., "Kidney-specific peptide-conjugated poly (ester amine) for the treatment of kidney fibrosis," Journal of Nanoscience and Nanotechnology, Jul. 2012, 12(7):5149-54.
Klassen et al., "Light chains are a ligand for megalin," Journal of Applied Physiology, Jan. 2005, 98(1):257-63.
Krebs et al., "Plasticity of Th17 cells in autoimmune kidney diseases," The Journal of Immunology, Jul. 2016, 197(2):449-57.
Kutscher et al., "Threshold size for optimal passive pulmonary targeting and retention of rigid microparticles in rats," Journal of Controlled Release, Apr. 2010, 143(1):31- 7.
Lan et al., "Local macrophage proliferation in the pathogenesis of glomerular crescent formation in rat anti-glomerular basement membrane (GBM) glomerulonephritis," Clinical & Experimental Immunology, Nov. 1997, 110(2):233-40.
Laurent et al., "Aminoglycoside-induced renal phospholipidosis and nephrotoxicity," Biochemical Pharmacology, Dec. 1990, 40(11):2383-92.
Li et al., "Aptamer-directed specific drug delivery and magnetic resonance imaging of renal carcinoma cells in vitro and in vivo," Journal of Biomedical Nanotechnology, Aug. 2016, 12(8):1604-16.
Liang et al., "Short-and long-term tracking of anionic ultrasmall nanoparticles in kidney," ACS Nano, Jan. 2016, 10(1):387-95.
Liu et al., "A tris (2-carboxyethyl) phosphine (TCEP) related cleavage on cysteine-containing proteins," Journal of the American Society for Mass Spectrometry, May 2010, 21:837-44.

(56) References Cited

OTHER PUBLICATIONS

Liu et al., "Comparison of sorafenib-loaded poly (lactic/glycolic) acid and DPPC liposome nanoparticles in the in vitro treatment of renal cell carcinoma," Journal of Pharmaceutical Sciences, Mar. 2015, 104(3):1187-96.
Liu et al., "Nanotechnology combined therapy: tyrosine kinase-bound gold nanorod and laser thermal ablation produce a synergistic higher treatment response of renal cell carcinoma in a murine model," BJU International, Feb. 2017, 119(2):342-8.
Lloyd et al., "Role of MCP-1 and Rantes in inflammation and progression to fibrosis during murine crescentic nephritis," Journal of Leukocyte Biology, Nov. 1997, 62(5):676-80.
Mahadevappa et al., "Megalin in acute kidney injury—foe and friend," American Journal of Physiology-Renal Physiology, Jan. 2014, 306(2):F147, 25 pages.
Meng et al., "Quantitative assessment of nanoparticle biodistribution by fluorescence imaging, revisited," ACS Nano, Jun. 2018, 12(7):6458-68.
Moeller et al., "Podocytes populate cellular crescents in a murine model of inflammatory glomerulonephritis," Journal of the American Society of Nephrology, Jan. 2004, 15(1):61-7.
Moghimi et al., "Nanomedicine: current status and future prospects," The FASEB Journal, Mar. 2005, 19(3):311-30.
Motzer et al., "Kidney cancer, version 3.2015," Journal of the National Comprehensive Cancer Network, Feb. 2015, 13(2):151-9.
Myatt et al., "Pathogenic potential of human monoclonal immunoglobulin light chains: relationship of in vitro aggregation to in vivo organ deposition," Proceedings of the National Academy of Sciences, Apr. 1994, 91(8):3034-8.
Nel et al., "New insights into "permeability" as in the enhanced permeability and retention effect of cancer nanotherapeutics," Acs Nano, Oct. 2017, 11(10):9567-9.
Nikzad et al., "Effects of radiofrequency radiation in the presence of gold nanoparticles for the treatment of renal cell carcinoma," Journal of Renal Injury Prevention, 2017, 6(2):103-8.
Nosko et al., "T-bet enhances regulatory T cell fitness and directs control of Th1 responses in crescentic GN," Journal of the American Society of Nephrology: JASN, Jan. 2017, 28(1):185-96.
Paust et al., "CXCR3+ regulatory T cells control TH1 responses in crescentic GN," Journal of the American Society of Nephrology: JASN, 2016, 27(7):1933-42.
Paust et al., "Regulatory T cells control the Th1 immune response in murine crescentic glomerulonephritis," Kidney International, Jul. 2011, 80(2):154-64.
PCT International Preliminary Report on Patentability in International Appln. No. PCT/US2021/054204, mailed on Mar. 28, 2023, 7 pages.
PCT International Search Report and Written Opinion in International Appln. No. PCT/US2021/054204, mailed on Feb. 23, 2022, 11 pages.
Piyaphanee et al., "Renal outcome and risk factors for end-stage renal disease in pediatric rapidly progressive glomerulonephritis," Pediatrics International, Mar. 2017, 59(3):334-41.
Ruggiero et al., "Paradoxical glomerular filtration of carbon nanotubes," Proceedings of the National Academy of Sciences, Jul. 2010, 107(27):12369-74.
Saito et al., "Complete cloning and sequencing of rat gp330/ "megalin," a Distinctive Member of the Low Density Lipoprotein Receptor Gene Family," Proceedings of the National Academy of Sciences, Oct. 1994, 91(21):9725-9.
Sanders, "Light chain-mediated tubulopathies," Experimental Models for Renal Diseases, 2011, 169:262-9.
Sanders, "Pathogenesis and treatment of myeloma kidney," The Journal of Laboratory and Clinical Medicine, Oct. 1994, 124(4):484-8.
Schuetz et al., "Molecular classification of renal tumors by gene expression profiling," The Journal of Molecular Diagnostics, May 2005, 7(2):206-18.
Shah et al., "Positive surgical margins increase risk of recurrence after partial nephrectomy for high risk renal tumors," The Journal of Urology, Aug. 2016, 196(2):327-34.
Shi et al., "Self-assembled targeted nanoparticles: evolution of technologies and bench to bedside translation," Accounts of Chemical Research, Oct. 2011, 44(10):1123-34.
Smaldone et al., "Small renal masses progressing to metastases under active surveillance: a systematic review and pooled analysis," Cancer, Feb. 2012, 118(4):997-1006.
Smeets et al., "Renal progenitor cells contribute to hyperplastic lesions of podocytopathies and crescentic glomerulonephritis," Journal of the American Society of Nephrology: JASN, Dec. 2009, 20(12):2593-603.
Smeets et al., "Tracing the origin of glomerular extracapillary lesions from parietal epithelial cells," Journal of the American Society of Nephrology: JASN, Dec. 2009, 20(12):2604-15.
Speed et al., "Recurrence in localized renal cell carcinoma: a systematic review of contemporary data," Current Urology Reports, Feb. 2017, 18:1-1.
Stewart et al., "Evaluation of the National Comprehensive Cancer Network and American Urological Association renal cell carcinoma surveillance guidelines," Journal of Clinical Oncology, Dec. 2014, 32(36):4059-65.
Sun et al., "Proximal tubular expression patterns of megalin and cubilin in proteinuric nephropathies," Kidney International Reports, Jul. 2017, 2(4):721-32.
Susantitaphong et al., "World incidence of AKI: a meta-analysis," Clinical journal of the American Society of Nephrology: CJASN, Sep. 2013, 8(9):1482-93.
Tipping et al., "T cells in crescentic glomerulonephritis," Journal of the American Society of Nephrology, May 2006, 17(5):1253-63.
Tipping et al., "The participation of macrophages, glomerular procoagulant activity, and factor VIII in glomerular fibrin deposition. Studies on anti-GBM antibody-induced glomerulonephritis in rabbits," The American Journal of Pathology, Jul. 1986, 124(1):10-7.
Turner et al., "Stahl RA. IL-17A production by renal γδ T cells promotes kidney injury in crescentic GN," Journal of the American Society of Nephrology: JASN, Sep. 2012, 23(9):1486-95.
Verroust et al., "Megalin and cubilin-the story of two multipurpose receptors unfolds," Nephrology Dialysis Transplantation, Nov. 2002, 17(11):1867-71.
Voss et al., "A randomized phase II trial of CRLX101 in combination with bevacizumab versus standard of care in patients with advanced renal cell carcinoma," Annals of Oncology, Nov. 2017, 28(11):2754-60.
Wang et al., "Anti-mouse CD52 monoclonal antibody ameliorates iron-deficient anaemia in IL-10 knockout mice," British Journal of Nutrition, Mar. 2014, 11(6):987-95.
Wang et al., "Design and in vivo characterization of kidney-targeting multimodal micelles for renal drug delivery," Nano Research, Oct. 2018, 11:5584-95.
Wang et al., Peptide and antibody ligands for renal targeting: nanomedicine strategies for kidney disease. Biomaterials science. 2017;5(8):1450, 26 pages.
Williams et al., "Mesoscale nanoparticles selectively target the renal proximal tubule epithelium," Nano Letters, Apr. 2015, 15(4):2358-64.
Williams et al., "Nanomedicines for kidney diseases," Kidney International, Oct. 2016, 90(4):740, 14 pages.
Wilson et al., "Anti-glomerular basement membrane antibody-induced glomerulonephritis," Kidney International, Feb. 1973, 3(2):74-89.
Xu et al., "Cancer nanomedicine: from targeted delivery to combination therapy," Trends in Molecular Medicine, Apr. 2015, 21(4):223, 20 pages.
Xu et al., "Comparisons of three polyethyleneimine-derived nanoparticles as a gene therapy delivery system for renal cell carcinoma," Journal of Translational Medicine, Dec. 2011, 9:46, 10 pages.
Yalcin et al., "Tetraidothyroacetic acid (tetrac) and tetrac nanoparticles inhibit growth of human renal cell carcinoma xenografts," Anticancer Research, Oct. 2009, 29(10):3825-31.

(56) References Cited

OTHER PUBLICATIONS

Yamada et al., "Mitochondrial delivery of doxorubicin using MITO-porter kills drug-resistant renal cancer cells via mitochondrial toxicity," Journal of Pharmaceutical Sciences, Sep. 2017, 106(9):2428-37.
Yang et al., "Cuprous oxide nanoparticles trigger ER stress-induced apoptosis by regulating copper trafficking and overcoming resistance to sunitinib therapy in renal cancer," Biomaterials, Nov. 2017, 146:72-85.
Ying et al., "Immunoglobulin light chains generate proinflammatory and profibrotic kidney injury," The Journal of Clinical Investigation, Jul. 2019, 129(7):2792, 47 pages.
Zhou et al., "Kidney—targeted drug delivery systems," Acta Pharmaceutica Sinica B, Feb. 2014, 4(1):37-42.
Zhuang et al., "Is caveolin involved in normal proximal tubule function? Presence in model PT systems but absence in situ," American Journal of Physiology-Renal Physiology, Jan. 2011, 300(1):F199, 39 pages.
Zuckerman et al., "siRNA delivery to the glomerular mesangium using polycationic cyclodextrin nanoparticles containing siRNA," Nucleic Acid Therapeutics, Apr. 2015, 25(2):53-64.
Zuckerman et al., "Targeting therapeutics to the glomerulus with nanoparticles," Advances in Chronic Kidney Disease, Nov. 2013, 20(6):500-7.

* cited by examiner

SEQUENCE LISTING

<160> NUMBER OF SEQ ID NOS: 7

<210> SEQ ID NO 1
<211> LENGTH: 106
<212> TYPE: PRT
<213> ORGANISM: Homo sapiens

<400> SEQUENCE: 1

Gly Gln Pro Lys Ala Asn Pro Thr Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Gly Ser Pro
35 40 45

Val Lys Ala Gly Val Glu Thr Thr Lys Pro Ser Lys Gln Ser Asn Asn
50 55 60

Lys Tyr Ala Ala Ser Ser Tyr Leu Ser Leu Thr Pro Glu Gln Trp Lys
65 70 75 80

Ser His Arg Ser Tyr Ser Cys Gln Val Thr His Glu Gly Ser Thr Val
85 90 95

Glu Lys Thr Val Ala Pro Thr Glu Cys Ser
100 105

<210> SEQ ID NO 2
<211> LENGTH: 106
<212> TYPE: PRT
<213> ORGANISM: Homo sapiens

<400> SEQUENCE: 2

Gly Gln Pro Lys Ala Ala Pro Ser Val Thr Leu Phe Pro Pro Ser Ser
1 5 10 15

Glu Glu Leu Gln Ala Asn Lys Ala Thr Leu Val Cys Leu Ile Ser Asp
20 25 30

Phe Tyr Pro Gly Ala Val Thr Val Ala Trp Lys Ala Asp Ser Ser Pro
35 40 45

Val Lys Ala Gly Val Glu Thr Thr Thr Pro Ser Lys Gln Ser Asn Asn
50 55 60

```
Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 3
<211> LENGTH: 106
<212> TYPE: PRT
<213> ORGANISM: Homo sapiens

<400> SEQUENCE: 3

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Ala Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 4
<211> LENGTH: 106
<212> TYPE: PRT
<213> ORGANISM: Homo sapiens

<400> SEQUENCE: 4

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105


<210> SEQ ID NO 5
<211> LENGTH: 107
<212> TYPE: PRT
<213> ORGANISM: Homo sapiens

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
            20                  25                  30

Tyr Pro Arg Glu Ala Lys Val Gln Trp Lys Val Asp Asn Val Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 6
<211> LENGTH: 107
<212> TYPE: PRT
<213> ORGANISM: Homo sapiens

<400> SEQUENCE: 6

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

KIDNEY TARGETED DELIVERY OF DRUGS

CLAIM OF PRIORITY

This application is the U.S. National Phase Application under 35 U.S.C. § 371 of International Patent Application No. PCT/US2021/054204, filed on Oct. 8, 2021, which claims the benefit of U.S. Provisional Patent Application No. 63/089,126, filed on Oct. 8, 2020, the contents of each of which are hereby incorporated by reference.

SEQUENCE LISTING

The present specification is being filed with a computer readable form (CRF) copy of the Sequence Listing. The CRF entitled 29618_0226W01_ST25.txt, which was created on Sep. 28, 2021 and is 7,086 bytes in size, is incorporated herein by reference in its entirety.

TECHNICAL FIELD

This invention relates to methods and compositions for targeted delivery of drugs to megalin-expressing tissues, such as kidneys.

BACKGROUND

The development of selective diagnostic and therapeutic agents that actively target the kidney (e.g., the proximal tubule epithelial cells (PTECs) of the kidney) has been hindered by significant difficulty. Nanomedicine, the delivery of these agents by the use of a nanoparticle (NP), offers an enticing solution to this predicament. The potential benefits of nanomedicine include improvement of the pharmacokinetics of an agent, minimization of systemic toxicity due to direct delivery of the agent to the affected site, maximization of the dosage of the agent at the site of action, and controlled or triggered release of the agent in a spatiotemporal manner.

The size, shape, and charge of a NP together affect its ability to localize to various compartments within the kidney, representing a significant barrier to its delivery to the kidney. The negatively charged slit diaphragm between the podocytes in the glomerulus and the intricate diaphragm that covers the fenestrations in renal peritubular capillaries contribute importantly to resisting the access of NPs to the tubules in the kidney.

Renal cell carcinoma (RCC) is the sixth most common cause of cancer in men and tenth in women in the United States. A prominent challenge faced by physicians caring for RCC patients is the high recurrence rate following treatment for localized disease, which ranges between 20-40%. Therefore, there is an unmet clinical need for the development of compositions that can specifically deliver diagnostic agents to the kidney.

SUMMARY

The present disclosure is based, at least in part, on the development of drug-containing polymeric particles that are targeted to megalin-expressing tissue (e.g., the kidneys). Megalin is a large type 1 transmembrane protein that belongs to the low-density lipoprotein receptor (LDLR) family; it is found on the apical surface of proximal tubule epithelial cells (PTECs), where it is responsible for the reclamation of a variety of filtered proteins from the urine. Megalin is also expressed by the clear cell subtype of renal cell carcinoma (RCC). The structure of megalin, as described initially in the rat, is defined by a large luminal portion that contains 36 LDLR ligand-binding complement-type repeat motifs grouped into 4 different domains.

The drug-containing polymeric particles of the disclosure are attached (linked, e.g., covalently conjugated) to one or more immunoglobulin light chains or megalin-binding fragments thereof. Without being bound by any particular theory, the one or more immunoglobulin light chains or megalin-binding fragments thereof bind to megalin, allowing for internalization of the drug-containing polymeric particle into the megalin-expressing cell and delivery of the drug to the cell.

The present disclosure provides, inter alia, compositions and methods useful for delivering drugs directly to the kidney (e.g., to the proximal tubule epithelial cells) and sites of kidney disease (e.g., renal cell carcinoma). In particular, the present disclosure provides compositions comprising the drug-containing polymeric nanoparticles described herein and methods using same.

In a first aspect, provided herein is a composition comprising: one or more drug-containing polymeric nanoparticles, each attached to one or more immunoglobulin light chains or a megalin-binding fragment thereof. In certain embodiments, the one or more immunoglobulin light chains or megalin-binding fragment thereof is a lambda immunoglobulin light chain or megalin-binding fragment thereof. In certain embodiments, the one or more drug-containing polymeric particles comprise an immunosuppressive or immunoregulatory drug.

In certain embodiments, the one or more drug-containing polymeric particles are each covalently conjugated to the one or more immunoglobulin light chains or megalin-binding fragment thereof. In certain embodiments, the one or more drug-containing polymeric particles are each attached to the one or more immunoglobulin light chains or megalin-binding fragment thereof through a linker.

In certain embodiments, the polymer comprises poly (lactic-co-glycolic) acid (PLGA), polylactide (PLA), or polyglycolide. In certain embodiments, the polymer comprises PLGA. In certain embodiments, the polymer comprises PLA. In certain embodiments, the polymer comprises polyglycolide.

In certain embodiments, the polymeric particle further comprises polyethylene glycol.

In certain embodiments, the composition further comprises a pharmaceutically acceptable carrier.

In a second aspect, provided herein is a method of delivering a drug to a kidney of a subject (e.g., a human), the method comprising administering any one of the foregoing compositions to the subject.

In a third aspect, provided herein is a method of delivering a drug to kidney tissue in a subject (e.g., a human), the method comprising administering any one of the foregoing compositions to the subject.

In a fourth aspect, provided herein is a method of treating a kidney disease in a subject (e.g., a human), comprising administering to the subject any one of the foregoing compositions. In some embodiments, the kidney disease is a kidney cancer.

In some embodiments, the kidney disease is renal cell carcinoma. In some embodiments, the kidney disease is crescentic glomerulonephritis. In some embodiments, the kidney disease is anti-glomerular basement membrane (GBM) disease. In some embodiments, the kidney disease is anti-neutrophil cytoplasmic antibody (ANCA)-associated vasculitis. In some embodiments, the kidney disease is immune complex glomerulonephritis.

In a fifth aspect, provided herein is a method of treating kidney injury in a subject, the method comprising: comprising administering to the subject any one of the foregoing compositions. In some embodiments, the drug-containing polymeric particle is delivered to proximal tubule epithelial cells in the subject. In some embodiments, the drug-containing polymeric particle is delivered to renal cell carcinoma cells in the subject. In some embodiments, the subject is a human. In some embodiments, the kidney injury is damage to the proximal tubule. In some embodiments, the kidney injury is ischemia-reperfusion injury. In some embodiments, the kidney injury is and toxicity from antibiotics.

In a sixth aspect, provided herein is a method of identifying renal cell carcinoma cells in a subject, comprising administering to the subject any one of the foregoing compositions, wherein the drug is a contrast agent or a dye.

In a seventh aspect, provided herein is any one of the foregoing compositions for use in treating or delaying the progression of a kidney disease in a subject. In some embodiments, the kidney disease is a kidney cancer. In some embodiments, the kidney disease is renal cell carcinoma. In some embodiments, the kidney disease is crescentic glomerulonephritis. In some embodiments, the kidney disease is anti-glomerular basement membrane (GBM) disease. In some embodiments, the kidney disease is anti-neutrophil cytoplasmic antibody (ANCA)-associated vasculitis. In some embodiments, the kidney disease is immune complex glomerulonephritis.

As used herein, the term "polymer" means a chemical species containing a plurality of repeating units that are bonded to each other. A polymer may contain more than one different repeating unit. The repeating unit typically derives from polymerization of a monomer. A copolymer specifically refers to a polymer containing two or more structurally different repeating units. The different repeating units of a polymer may be randomly ordered in the polymer chain or the same repeating units may be grouped into contiguous blocks in the polymer. When there are contiguous blocks of the two or more repeating units in a polymer, the polymer is a block copolymer.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient of the symptoms, that can be attributed to or associated with treatment by the compositions and methods of the present disclosure.

The terms "effective amount" and "effective to treat," as used herein, refer to an amount or a concentration of one or more of the compositions described herein utilized for a period of time (including acute or chronic administration and periodic or continuous administration) that is effective within the context of its administration for causing an intended effect or physiological outcome.

The term "subject" is used throughout the specification to describe an animal, human or non-human, rodent or non-rodent, to whom treatment according to the methods of the present disclosure is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1A: Representative transmission electron micrograph of LC-NP, negatively stained and imaged at 80.0 kV (scale bar: 50 nm), reveals its uniform spherical shape. FIG. 1B: Exposure of HK-2 cells to LC-NP for 2, 6, and 24 hours demonstrates no significant difference between time points in viability, as measured by flow cytometry (n=4). FIG. 1C: Incubation of HK-2 cells with either NP or LC-NP, or no agent (Ctrl) for 24 hours, demonstrated no significant difference in viability (n=4). FIG. 1D: Representative fluorescence micrographs at low and high magnification of a murine kidney demonstrate expression of megalin by the proximal tubules, situated along their apical surface. Sections were also stained with glomerular marker PDPN and nuclear marker 4',6-diamidino-2-phenylindole (DAPI). FIG. 1E-FIG. 1G: Fluorescence micrographs of HK-2 cells incubated with (FIG. 1E) NP and (FIG. 1F) LC-NP for 1 hour showed a significantly higher accumulation of LC-NP in comparison to NP (FIG. 1G). Cells were stained for megalin and with nuclear marker DAPI (*$P<0.05$; n=3/group, calculated by two-tailed Student's t-test).

FIG. 1H: Exposure of HK-2 cells to LC-NPs for 6, 24, 48, and 72 hours demonstrated no significant difference in viability between the time points, as measured by MTT assay (n=8 replicates/condition). FIG. 1I: Incubation of HK-2 cells with different concentration of either NPs (left column for each concentration) or LC-NPs (right column for each concentration) for 24 hours demonstrated no significant difference in viability, as assessed by MTT assay (n=8 replicates/condition). The data are representative of 2 independent MTT assays.

FIG. 2A-FIG. 2B: Representative ex vivo images of murine kidneys at 1 day, 2 days, 7 days, and 28 days (from top to bottom in FIG. 2A, respectively, and from left to right, respectively, in FIG. 2B) following intravenous injection of IR800-labeled NP or LC-NP (FIG. 2A) demonstrate significantly higher signal of kidneys from mice injected with LC-NP in comparison to NP, as indicated by mean fluorescence intensity (MFI) (FIG. 2B). Values are means±SD. (***$P<0.005$, n=3-4/group, calculated by two-tailed Student's t-test). FIG. 2C-FIG. 2F: Fluorescence micrographs of kidneys harvested from mice 24 hours following injection of LC-NP demonstrates its localization to the proximal tubule, as indicated by staining with vascular marker CD31 (FIG. 2C), glomerular marker PDPN (FIG. 2D), and proximal tubular markers LTL (FIG. 2E) as well as megalin (FIG. 2F).

FIG. 3A: Light micrograph of H&E-stained kidney tissues harvested from LC-NP and NP-treated mice at 1, 7 and 28 days following injection reveals normal glomerular and tubular architecture. FIG. 3B: Representative image of immunofluorescence staining for KIM1 staining in kidney at day 7 post injection, demonstrated no sign of damage in proximal tubular architecture of the kidney tissues. FIG. 3C: Representative image of light micrograph of H&E-stained kidney tissue from repetitive injection of LC-NP revealed no change in morphology. FIG. 3D: Representative image of immunofluorescence staining for KIM1 staining in kidney tissue from repetitive injection of LC-NP revealed no sign of damage in proximal tubular architecture of the kidney tissues.

FIG. 4A: Transmission electron micrograph of urine immediately after intravenous injection of LC-NP demonstrates presence of LC-NP. FIG. 4B-FIG. 4C: Representative fluorescence micrographs of kidney immediately after injection with LC-NP demonstrate distribution in glomerulus and proximal tubules, as indicated by staining with glomerular marker PDPN (FIG. 4B) and co-staining with glomerular marker PDPN, proximal tubule marker megalin, and nuclear marker DAPI (FIG. 4C). FIG. 4D-FIG. 4F: Representative ex vivo images of kidneys from mice treated with (FIG. 4D) vehicle (DPBS), and (FIG. 4E) cilastatin demonstrate significantly higher MFI in the kidneys from those treated with DPBS (FIG. 4F). Values are means±SD. (*$P<0.05$ n=4/group, calculated by two-tailed Student's t-test).

FIG. 4G: MFI of the kidneys from mice treated with either cilastatin or vehicle demonstrating significantly higher MFI in the kidneys from those treated with DPBS (n=3-7/group). FIG. 4H: LC-NPs underwent lower uptake by HK-2 cells treated with cilastatin than vehicle (DPBS)-treated cells. FIG. 4I: HK-2 cells treated with megalin siRNA also exhibited lower uptake of LC-NPs in comparison to those treated with control siRNA. Values are means±SD. means±SD. $P<0.01$, and *$P<0.001$ and ns: not significant as calculated by two-tailed Student's t-test.

FIG. 5A-FIG. 5B: MFI of kidneys containing renal cell carcinoma at 1, 2, 3 days (from left to right, respectively, in FIG. 5A, or from top to bottom, respectively, in FIG. 5B) following intravenous injection of either NP or LC-NP in tumor-bearing mice demonstrates significantly higher signal in LC-NP-injected mice compared to NP-injected mice. Values are means±SD. (**$P<0.01$, n=3-4/group, calculated by two-tailed Student's t-test). FIG. 5B: Representative images of tumors from sacrificed mice at different time points. FIG. 5C: Representative fluorescence micrograph of tumor tissue exhibits co-localization of LC-NP with megalin-expressing cells in tumor tissue. Nuclear marker DAPI. FIG. 5D: Fluorescence micrograph of human renal cell carcinoma depicts high expression of megalin in the tumor. Nuclear marker DAPI. FIG. 5E: A representative fluorescence micrograph of human DLN depicts high expression of megalin (green) in clearly demarcated metastatic lesions of RCC (asterisks).

FIG. 5F: Representative photograph and ex vivo image demonstrating MFI of kidney with RCC (on right) and contralateral kidney without RCC (on left) 24 hours following injection of LC-NPs. FIG. 5G: MFI of the kidney-draining lymph nodes (DLNs) of the RCC tumor-bearing mice confirms higher retention of LC-NPs compared to unconjugated NPs at 3 days post-injection. FIG. 5H: DLNs exhibit higher signal compared to NDLNs at 3 days following injection of LC-NPs. (n=3-4/group)

FIG. 6A: Ex vivo imaging depicting biodistribution of vehicle (DPBS), NP, and LC-NP to various organs at 24 hours following intravenous injection in C57BL/6 mice reveals that LC-NP accumulates in the kidneys, lung, and liver to a greater extent in comparison to NP. FIG. 6B-FIG. 6D: Accumulation of LC-NP in proximal tubules of kidney at (FIG. 6B) 24 hours, (FIG. 6C) 48 hours, and (FIG. 6D) 7 days following intravenous injection. Proximal tubule marker LTL and Nuclear marker DAPI. FIG. 6E: Fluorescence micrograph of IR-800 loaded LC-MP reveals its spherical shape. FIG. 6F: Biodistribution of MP and LC-MP at 24 hours post-injection in C57BL/6 mice reveals nearly exclusive accumulation of MP in the lung compared to other major organs.

FIG. 8A: TEM image of the urine from a naïve mouse. FIG. 8B: Representative fluorescence micrograph of Renca cells stained for megalin (green) and with nuclear marker DAPI (blue). FIG. 8C: High expression of megalin (green) in RCC tumors from human patients, other than that visualized in FIG. 5 (n=4 patients). FIG. 8D: High expression of megalin (green) in metastatic lesions of RCC in DLNs from human patients, other than that visualized in FIG. 5 (n=4 patients).

DETAILED DESCRIPTION

Figures 1A, 1B, 1C, 1D, 1E, 1F, 1G:
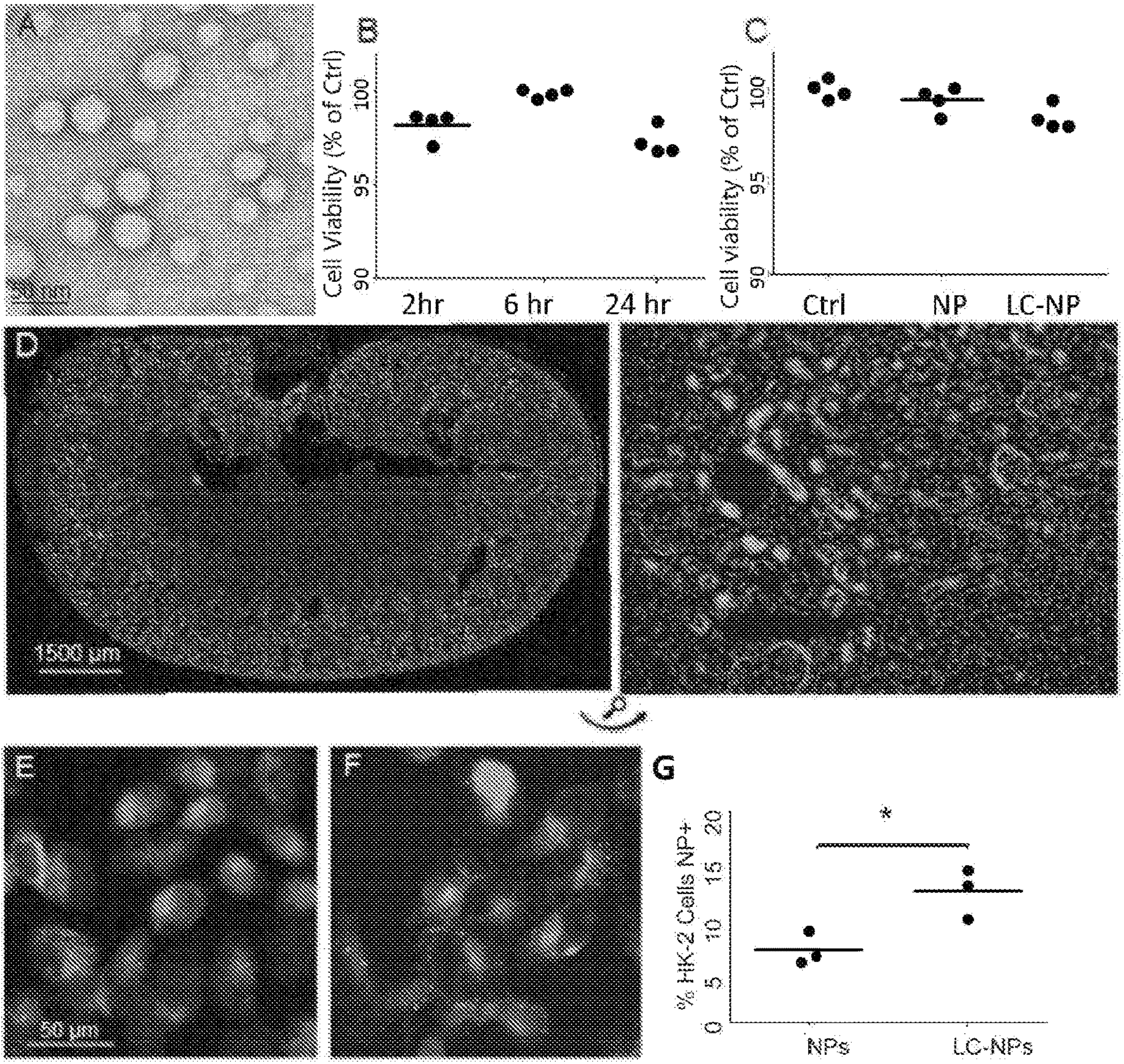
FIG. 1A-FIG. 1G. Light chain nanoparticle (LC-NP) is internalized by megalin-expressing proximal tubule epithelial cells in vitro.

The field of nanomedicine constitutes a promising new frontier in nephrology research. The development of targeted drug carriers to the kidney can alter fundamentally the management of patients with renal disease, since current treatment modalities for primary renal disorders often employ drugs that exert potent off-target effects. A major unmet need for the development of kidney-targeted nanomedicine pervades the practice of clinical nephrology, as acute kidney injury affects up to 20% of all hospitalized patients worldwide. However, currently no pharmacologic treatment exists for renal damage resulting from dysfunction of the proximal tubule due to ischemia-reperfusion injury, sepsis, or drug-related toxicity, which are common causes for acute kidney injury.

This disclosure is based, in part, on the synthesis of a light-chain conjugated NP (LC-NP) that was designed to target the membrane protein megalin, which is expressed both by the proximal tubular epithelium in the kidney as well as renal cell carcinoma cells. As demonstrated herein, these LC-NPs localized selectively to both of these cell types in vitro and in vivo. The LC-NPs remained in the kidneys for at least 7 days following a single injection, reinforcing a major advantage of these constructs: retention of the payload at its intended site of action, long after its administration. Without being bound by any particular theory, this property of LC-NP could reduce effectively the dosing of the agent that it delivers, an important feature that may limit the off-target toxicity of the encapsulated agent.

The specific delivery and retention of LC-NP to the proximal tubule of the kidney in comparison to other organs that contain megalin, such as lung and liver, demonstrate its applicability as a therapeutic vehicle for forms of kidney injury caused by damage to the proximal tubule, such as ischemia-reperfusion injury and toxicity from antibiotics, like aminoglycosides and possibly vancomycin.40, 41 This usage could assist in solving a significant unmet clinical need in the field of nephrology by concentrating the delivery of drugs developed in the future to treat these diseases at their intended site of action. Moreover, the field of nanomedicine contains a dearth of in vivo studies that have demonstrated the successful active targeting to PTECs of nanoparticles conjugated with a molecular recognition entity42. Hence, LC-NP demonstrates remarkable potential as a kidney-targeted drug carrier that not only delivers a concentrated therapeutic payload to PTECs, but also optimizes pharmacokinetics due to its persistence in the kidney.

The functional versatility of LC-NP is underlined by its selective trafficking to RCC. The recommendations for schedule of imaging following local resection of the primary tumor released by the National Comprehensive Cancer Network46 and American Urological Association47 result in identification of just 68.2% and 66.9% of recurrent lesions, 48 respectively. In addition, the majority (~83%) of recurrent disease presents in patients within 5 years following resection49. The main sites of recurrence are the lung (52-64% of cases) and bone (9-15%)[49]-51. Hence, a non-invasive method of identification for subclinical RCC lesions that evade detection by the typical imaging techniques currently in use at the time of diagnosis is sorely needed. Injection of LC-NPs containing the corresponding contrast media or dye prior to the imaging study may improve this capability. Therefore, LC-NP may augment the sensitivity of surveillance imaging performed for detection of recurrence, and for active monitoring of tumors in patients deemed to be at prohibitively high surgical risk52 or for those at high risk of recurrence due to positive surgical margins53.

Several previous investigations of NP-assisted therapy for RCC have been conducted54-69. However, all except one64 of these studies rely on the enhanced permeability and retention (EPR) effect, whereby NPs accumulate at the tumor site due to increased leakiness of the surrounding vasculature70. Therefore, a significant void in this scientific field remains unfilled for more elegant and specifically targeted techniques of therapeutic delivery to RCC. LC-NP can also provide a solution to the lack of specificity for therapeutics in this area.

In summary, LC-NP, a nanocarrier with the capability for the first time to target selectively both the PTECs of the kidney and RCC through the binding of light chains to megalin, were synthesized. Currently unmet, exigent clinical needs exist for the treatment of kidney injuries that arise from toxicity to the proximal tubule as well as for improvement in the sensitivity of imaging techniques for the detection of RCC. Thus, LC-NP demonstrates great potential for use in the diagnosis and treatment of both non-oncologic and oncologic disorders that arise from the kidney.

The present disclosure is based, at least in part, on the development of drug-containing polymeric particles that are targeted to megalin-expressing tissue (e.g., the kidneys). Megalin is a large type 1 transmembrane protein that belongs to the low-density lipoprotein receptor (LDLR) family; it is found on the apical surface of proximal tubule epithelial cells (PTECs), where it is responsible for the reclamation of a variety of filtered proteins from the urine. Megalin is also expressed by the clear cell subtype of renal cell carcinoma (RCC). The structure of megalin, as described initially in the rat, is defined by a large luminal portion that contains 36 LDLR ligand-binding complement-type repeat motifs grouped into 4 different domains.

The drug-containing polymeric particles of the disclosure are attached (linked, e.g., covalently conjugated) to one or more immunoglobulin light chains or megalin-binding fragments thereof. Without being bound by any particular theory, the one or more immunoglobulin light chains or megalin-binding fragments thereof bind to megalin, allowing for internalization of the drug-containing polymeric particle into the megalin-expressing cell and delivery of the drug to the cell.

The present disclosure provides, inter alia, compositions and methods useful for delivering drugs directly to the kidney (e.g., to the proximal tubule epithelial cells) and sites of kidney disease (e.g., renal cell carcinoma).

The compositions disclosed herein include one or more drug-containing polymeric particles, each of which are attached to an immunoglobulin light chain or a megalin-binding fragment thereof.

Also provided herein are methods of using the drug-containing polymeric particles, such as, methods of delivering one or more drugs to a kidney or kidney tissue of a subject, treating a kidney disease in a subject, and delaying the progression of a kidney disease in a subject. Each of the foregoing methods comprises administering to the subject a drug-containing polymeric particle (or composition thereof) described herein. In some embodiments, the subject is a human.

Drug-Containing Polymeric Nanoparticles

The nanoparticles described herein can be made of materials that (i) are biocompatible, i.e., do not cause a significant adverse reaction in a living animal when used in pharmaceutically relevant amounts; (ii) feature functional groups to which an immunoglobulin light chain or megalin-binding fragment thereof can be covalently attached, (iii) exhibit low non-specific binding to other molecules, and (iv) are stable in solution, i.e., the particles do not precipitate. The particles can be monodisperse (a single crystal of a material, e.g., a metal, per particle) or polydisperse (a plurality of crystals, e.g., 2, 3, or 4, per particle).

A number of biocompatible polymers suitable for use in the production of the drug-containing polymeric nanoparticles described herein are known in the art, e.g., poly(lactic-co-glycolic) acid (PLGA), polylactide, and polyglycolide. In a specific embodiment, the one or more drug-containing polymeric particle comprises a PLGA polymer. In a specific embodiment, the one or more drug-containing polymeric particle comprises a polylactide polymer. In a specific embodiment, the one or more drug-containing polymeric particle comprises a polyglycolide polymer.

In some embodiments, the drug-containing polymeric particles can be poly(ethyleneglycol)ated (PEGylated), e.g., as described in U.S. Pat. Nos. 7,291,598; 5,145,684; 6,270,806; 7,348,030, and others, to reduce blood protein binding, and/or liver and spleen uptake. For example, in some embodiments, the one or more drug-containing polymeric particle comprises a PEGylated PLGA polymer. In another example, the one or more drug-containing polymeric particle comprises a PEGylated polylactide polymer. In yet another example, the one or more drug-containing polymeric particle comprises a PEGylated polyglycolide polymer. PEGylation creates stealth-like structures to bypass immune recognition by macrophage cells, thus achieving suppressed opsonization and enhanced retention of the particles in circulation. Such simple surface modification, e.g., pegylation, can increase the circulation half-life of a particle from several minutes to several or tens of hours.

In all embodiments, the polymeric nanoparticles are attached (linked, e.g., covalently conjugated) to one or more immunoglobulin light chains or a megalin-binding fragments thereof. The one or more immunoglobulin light chains or megalin-binding fragments thereof may be attached to the nanoparticles via functional groups of the polymer of the polymeric nanoparticle. For example, the one or more immunoglobulin light chains or megalin-binding fragments thereof may be conjugated to the drug-containing polymeric particles In other embodiments, the nanoparticles are associated with non-polymeric functional group compositions. Methods are known to synthesize stabilized, functionalized nanoparticles. Such methods are described, for example, in Halbreich et al., Biochimie, 80 (5-6):379-90, 1998.

In some embodiments, a drug (e.g., an immunosuppressive or immunoregulatory drug) described herein can be encapsulated within, e.g., mixed within or under a coating of, the nanoparticles. In some embodiments, a drug (e.g., an immunosuppressive or immunoregulatory drug) described herein can be conjugated with, e.g., outside the surface of, the nanoparticles.

Immunosuppressive or Immunoregulatory Drugs

Nonlimiting examples of drugs that may be incorporated into the drug-containing nanoparticles described herein include cyclophosphamide, a corticosteroid, cyclosporine A, rapamycin, Tacrolimus, mycophenolate, mofetil, cyclosporine, fingolimod, myriocin, checkpoint inhibitors (e.g., anti-CTLA-4 antibodies, anti-PD1 antibodies, anti-PDL1 antibodies), anti-inflammatory agents (e.g., anti-TNF drugs, such as, e.g., adalimumab), chemotherapeutic agents, and monoclonal antibodies such as anti-CD52 antibody, anti-CD3 antibody, anti-CD25 antibody, anti-IL6 antibody, CTLA-4-Ig, and adalimumab.

In some embodiments, the drug of the drug-containing particle is cyclophosphamide. In some embodiments, the drug of the drug-containing particle is a corticosteroid (e.g., cortisol, corticosterone, cortisone, or aldosterone). In some embodiments, the drug of the drug-containing particle is an anti-CD52 antibody (e.g., alemtuzumab). In some embodiments, the drug of the drug-containing particle is rapamycin.

In some embodiments, the immunosuppressive or immunoregulatory drugs have one or more hydroxyl groups or thiol groups and can function as polymerization initiators in the presence of certain catalysts.

Synthesis of Drug-Containing Polymeric Nanoparticles

There are a variety of ways that the drug-containing nanoparticles can be prepared, but in all methods, the result must be a particle with functional groups that can be used to link the particle to an immunoglobulin light chain or a megalin-binding fragment thereof.

In some embodiments, a drug-containing polymeric nanoparticle described herein is synthesized as described in the working examples below (see Example 1).

In some embodiments, a drug (e.g., an immunosuppressive or immunoregulatory drug) described herein can be encapsulated within, e.g., mixed within or under a coating of, the nanoparticles. Such drug-encapsulated nanoparticles can be synthesized using a nanoprecipitation method, e.g., described in Tang, L., et al., J. Transplantation, 2012: 896141, 2012, the content of which is incorporated by reference herein. Briefly, a drug to be delivered and PEGylated polymers can be dissolved in a suitable organic solvent. The resulting solution can be added dropwise into a nonsolvent, e.g., water, under vigorous stirring to form PEGylated drug-encapsulated polymeric nanoparticles. The particle suspension can then be stirred at room temperature to evaporate the organic solvent. An aliquot of the particle suspension can be centrifuged and the supernatant can be analyzed, e.g., by a reverse phase HPLC, to determine the incorporation efficiency and loading of the drug into the nanoparticles. The nanoparticles can then be purified and collected, e.g., by ultrafiltration. Optionally, a lyoprotectant, e.g., bovine serum albumin (BSA), can be added to the particle solution, which can then be lyophilized and stored at −20° C. The size and polydispersity of the resulting nanoparticles can be determined by dynamic light scattering (DLS) and/or scanning electron microscope (SEM).

In some embodiments, a drug (e.g., an immunosuppressive or immunoregulatory drug) described herein can be conjugated with, e.g., outside the surface of, the nanoparticles. Such drug-conjugated nanoparticles can be synthesized using methods described in e.g., Azzi, J., et al., FASEB J 24: 3927-3938, 2010, or in the international application publication WO 2008/109483, the contents of which are incorporated by reference herein. Briefly, a drug to be delivered can be mixed with one or more cyclic monomers and a catalyst in a suitable solvent. The drug serves as an initiator in a ring-opening polymerization reaction to form drug-polymer conjugates in which the drug is covalently bonded to the polymer. Because the drug is used as the initiator of polymerization, the efficiency of conjugation of the drug to the polymer is very high, and the drug-loading percentage can be controlled by adjusting the monomer/initiator ratio. The drug-polymer conjugates and PEGylated polymers can then be added dropwise into a nonsolvent, e.g., water, under vigorous stirring to form PEGylated drug-conjugated polymeric nanoparticles. The particle suspension can then be stirred at room temperature to evaporate the organic solvent. The nanoparticles can be purified and collected, e.g., by ultrafiltration. Optionally, a lyoprotectant, e.g., bovine serum albumin (BSA), can be added to the particle solution, which can then be lyophilized and stored at −20° C. The size and polydispersity of the resulting nanoparticles can be determined by dynamic light scattering (DLS) and/or scanning electron microscope (SEM).

Suitable monomers for the ring-opening polymerization include various cyclic monomers, e.g., cyclic esters, cyclic carbonates, cyclic siloxanes, cyclic phosphates, cyclic peptides or amino acid derivative, or cyclic phosphazanes. Exemplified cyclic monomers include lactide or glycolide.

The polymeric nanoparticles described herein can be used to deliver any small molecule drug that contains at least one functional group capable of initiating the ring-opening polymerization reaction, e.g. a hydroxyl group or a thiol group. The drug may contain a plurality of such polymerization initiation groups, e.g., a plurality of hydroxyl groups or thiol groups. In some embodiments, the drug contains only one of such polymerization groups. The hydroxyl groups may be primary, secondary or tertiary hydroxyl groups. Similarly, the thiol groups may be primary, secondary or tertiary thiol groups. The hydroxyl group may also be a phenolic hydroxyl group. In some embodiments, the drug contains one or more non-phenolic hydroxyl groups. In some embodiments, the drug contains one or more non-phenolic hydroxyl groups that are primary or secondary hydroxyl groups. In some embodiments, the drug contains a single nonphenolic hydroxyl group. In some embodiments, the drug contains a single primary or secondary hydroxyl group. In some embodiments, the immunosuppressive or immunoregulatory drugs having one or more hydroxyl groups or thiol groups function as polymerization initiators in the presence of certain catalysts.

A number of catalysts can be employed to facilitate formation of the drug-containing polymeric nanoparticles. Exemplary catalysts include numerous metal-oxides (M-ORs) and alcohol-metal oxides (RO-M) developed for controlled, living polymerization of cyclic monomers (O. Dechy-Cabaret, B. Martin-Vaca, & D. Bourissou, Chemical Reviews 104: 6147-6176, 2004). Metal-oxides can be prepared in situ by mixing a hydroxyl-containing compound with an active metal complex, such as a metal-amido compound (B. M. Chamberlain, M. Cheng, D. R. Moore, T. M. Ovitt, E. B. Lobkovsky, G. W. Coates, J. Am. Chem. Soc. 123: 3229, 2001). For example, (BDI)MgN$(TMS)_2$, a very active catalyst for the polymerization of lactide, can be employed (Chamberlain, 2001). Certain Zn catalysts, e.g., (BDI)ZnN$(TMS)_2$, facilitate fast initiation and relatively slow chain propagation, and can be used as catalyst for the polymerization. Zn-mediated lactide polymerization can result in polymers with narrow polydispersity. Other useful catalysts include Ca and Fe catalysts. Since Mg, Zn, Ca, and Fe are elements found in human body, catalysts containing these elements have a better safety profile than other active catalysts containing Al and Sn. Exemplary Zn, Mg, Ca and Fe catalysts, include the organocatalysts are described in WO 2008/109483. In some embodiments, a Zn catalyst, e.g., (BDI)ZnN(TMS)2, is used to initiate the drug-containing polymeric nanoparticles.

The nanoparticles described herein have shown high drug loading (about 50%) and loading efficiency (98-100%), well-controlled drug release kinetics without a burst release effect and excellent controlled particle size with a very narrow size distribution (Tong, R. & Cheng, J., Angew. Chem., Int. Ed. 47: 4830-4834, 2008; Tong, R. & Cheng, J., J. Am. Chem. Soc. 131: 4744-4754, 2009).

Particle size can be controlled by adjusting reaction conditions, for example, by varying temperature as described in U.S. Pat. No. 5,262,176. Uniform particle size materials can also be made by fractionating the nanoparticles using centrifugation, ultrafiltration, or gel filtration, as described, for example in U.S. Pat. No. 5,492,814.

In some embodiments, the drug-containing polymeric nanoparticles described herein are spherical. In some embodiments, the diameter of a drug-containing polymeric nanoparticle described herein is less than 90 nm. In some embodiments, the diameter of a drug-containing polymeric nanoparticle described herein is less than 80 nm. In some embodiments, the diameter of a drug-containing polymeric nanoparticle described herein is less than 60 nm. In some embodiments, the diameter of a drug-containing polymeric nanoparticle described herein is less than 50 nm. In some embodiments, the diameter of a drug-containing polymeric nanoparticle described herein is less than 25 nm. In some embodiments, the diameter of a drug-containing polymeric nanoparticle described herein is less than 10 nm. In some embodiments, the diameter of a drug-containing polymeric nanoparticle described herein is about 5 nm, about 10 nm, about 20 nm, about 30 nm, about 40 nm, about 50 nm, about 60 nm, about 70 nm, about 80 nm, about 90 nm, or about 100 nm. In some embodiments, the size of a drug-containing polymeric nanoparticle described herein is 2 nm to 100 nm, 2 to 90 nm, 2 to 80 nm, 2 to 70 nm, 2 to 60 nm, 2 to 50 nm, 2 to 25 nm, 2 to 10 nm, or 2 to 5 nm. In some embodiments, the diameter of a drug-containing polymeric nanoparticle described herein is 2 to 80 nm. In some embodiments, the diameter of a drug-containing polymeric nanoparticle described herein is 2 to 60 nm. In some embodiments, the diameter of a drug-containing polymeric nanoparticle described herein is 2 to 10 nm. In some embodiments, the diameter of a drug-containing polymeric nanoparticle described herein is 10 to 80 nm. In some embodiments, the diameter of a drug-containing polymeric nanoparticle described herein is 10 to 60 nm. In some embodiments, the diameter of a drug-containing polymeric nanoparticle described herein is 10. In some embodiments, the diameter of a drug-containing polymeric nanoparticle described herein is 60 nm. In some embodiments, the diameter of a drug-containing polymeric nanoparticle described herein is 80 nm. In some embodiments, the drug-containing polymeric nanoparticles have an overall diameter in the 2-80 nm range and are particularly useful for delivery to kidney cells (e.g., proximal tubule epithelial cells). When describing the diameter of the drug-containing polymeric nanoparticle, it is to be understood that the diameter is the diameter of the particle when conjugated to the one or more immunoglobulin light chains or megalin-binding fragments thereof.

In some embodiments, the drug-containing polymeric nanoparticles disclosed herein can be surface-modified to provide functional groups that can be used to link the nanoparticles to the immunoglobulin light chain or megalin-binding fragment thereof. For example, the nanoparticles can be functionalized according to a version of the method of Albrecht et al., Biochimie, 80(5-6): 379-90, 1998. Dimercapto-succinic acid can be coupled to the nanoparticles and provides a carboxyl functional group. By functionalized is meant the presence of amino or carboxyl or other reactive groups that can be used to attach desired moieties (e.g., the immunoglobulin light chain or megalin-binding fragment thereof) to the nanoparticles. In some embodiments, the immunoglobulin light chains or megalin-binding fragments thereof are conjugated to the drug-containing polymeric nanoparticles via covalent conjugation of maleimide groups on the surface of the polymeric nanoparticles to sulfydryl groups on the immunoglobulin light chains or megalin-binding fragments thereof. In some embodiments, the immunoglobulin light chains or megalin-binding fragments thereof are conjugated to the drug-containing polymeric nanoparticles via covalent conjugation of maleimide-PEG-amine groups on the surface of the polymeric nanoparticles to sulfydryl groups on the immunoglobulin light chains or megalin-binding fragments thereof.

Carboxyl functionalized nanoparticles can be made, for example, according to the method of Gorman (see WO 00/61191). Carboxyl-functionalized nanoparticles can also be made from polysaccharide coated nanoparticles by reaction with bromo or chloroacetic acid in strong base to attach carboxyl groups. In addition, carboxyl-functionalized nanoparticles can be made from amino-functionalized nanoparticles by converting amino to carboxyl groups by the use of reagents such as succinic anhydride or maleic anhydride. Carboxyl-functionalized nanoparticles can be converted to amino-functionalized magnetic nanoparticles by the use of water-soluble carbodiimides and diamines such as ethylene diamine or hexane diamine.

Nanoparticles can also be treated with periodate to form aldehyde groups. The aldehyde-containing nanoparticles can then be reacted with a diamine (e.g., ethylene diamine or hexanediamine), which will form a Schiff base, followed by reduction with sodium borohydride or sodium cyanoborohydride.

Dextran-coated nanoparticles can also be made and cross-linked, e.g., with epichlorohydrin. The addition of ammonia will react with epoxy groups to generate amine groups, see Hogemann et al., Bioconjug. Chem. 2000. 11(6):941-6, and Josephson et al., Bioconjug. Chem., 1999, 10(2):186-91.

Avidin or streptavidin can be attached to nanoparticles for use with a biotinylated binding moiety, such as an oligonucleotide or polypeptide. See e.g., Shen et al., Bioconjug. Chem., 1996, 7(3):311-6. Similarly, biotin can be attached to a particle for use with an avidin-labeled binding moiety.

In some embodiments, the drug-containing polymeric nanoparticles can be poly(ethyleneglycol)ated (PEGylated), e.g., as described in U.S. Pat. Nos. 7,291,598; 5,145,684; 6,270,806; 7,348,030, and others, to reduce blood protein binding, and/or liver and spleen uptake. For example, in some embodiments, the one or more drug-containing polymeric particle comprises a PEGylated poly(lactic-co-glycolic) acid polymer. In another example, the one or more drug-containing polymeric particle comprises a PEGylated polylactide polymer. In yet another example, the one or more drug-containing polymeric particle comprises a PEGylated polyglycolide polymer. PEGylation creates stealth-like structures to bypass immune recognition by macrophage cells, thus achieving suppressed opsonization and enhanced retention of the nanoparticles in circulation. Such simple surface modification, e.g., PEGylation, can increase the circulation half-life of a particle from several minutes to several or tens of hours.

Light Chain-Conjugated Drug-Containing Particles

To target the drug-containing polymeric nanoparticles to specific kidney tissues, the nanoparticles disclosed herein can be coated with an immunoglobulin light chain or megalin-binding fragment thereof.

In some embodiments, the immunoglobulin light chain is a human immunoglobulin light chain.

In some embodiments, the light chain is a lambda immunoglobulin light chain (e.g., a human lambda immunoglobulin light chain). Each individual human includes between seven and eleven different lambda light chain genes, which encode light chains selected from Lambda1, Lambda2, Lambda3, Lambda4, Lambda5, Lambda6, and Lambda7. In particular embodiments, the light chain is a lambda light chain selected from Lambda1, Lambda2, Lambda3, Lambda4, Lambda5, Lambda6, and Lambda7. In particular embodiments, the light chain is a lambda light chain selected from Lambda1, Lambda2, Lambda3, and Lambda 7. In particular embodiments, the light chain is an IgG1 lambda light chain comprising one of the following amino acid sequences:

```
IGLC1:
                                            (SEQ ID NO: 1)
GQPKANPTVTLFPPSSEELQANKATLVCLISDFYPGAVTVAWKADGSPV
KAGVETTKPSKQSNNKYAASSYLSLTPEQWKSHRSYSCQVTHEGSTVE
KTVAPTECS;

IGLC2:
                                            (SEQ ID NO: 2)
GQPKAAPSVTLFPPSSEELQANKATLVCLISDFYPGAVTVAWKADSSPV
KAGVETTTPSKQSNNKYAASSYLSLTPEQWKSHRSYSCQVTHEGSTVE
KTVAPTECS;

IGLC3:
                                            (SEQ ID NO: 3)
GQPKAAPSVTLFPPSSEELQANKATLVCLISDFYPGAVTVAWKADSSPA
KAGVETTTPSKQSNNKYAASSYLSLTPEQWKSHKSYSCQVTHEGSTVE
KTVAPTECS;
or

IGLC7:
                                            (SEQ ID NO: 4)
GQPKAAPSVTLFPPSSEELQANKATLVCLVSDFYPGAVTVAWKADGSP
```

-continued

```
VKVGVETTKPSKQSNNKYAASSYLSLTPEQWKSHRSYSCRVTHEGSTV
EKTVAPAECS.
```

In some embodiments, the light chain is an IgG1 lambda light chain comprising an amino acid sequence having at least 80%, at least 85%, at least 90%, at least 95%, or at least 97% identity to any one of SEQ ID NOs:1-4.

As known in the art, "sequence identity" between two polypeptides or two polynucleotides is determined by comparing the amino acid or nucleic acid sequence of one polypeptide or polynucleotide to the sequence of a second polypeptide or polynucleotide. When discussed herein, whether any particular polypeptide is at least about 40%, 45%, 50%, 55%, 60%, 65%, 70%, 75%, 80%, 85%, 90% or 95% identical to another polypeptide can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, WI 53711). BESTFIT uses the local homology algorithm of Smith and Waterman, Advances in Applied Mathematics 2 (1981), 482-489, to find the best segment of homology between two sequences. When using BESTFIT or any other sequence alignment program to determine whether a particular sequence is, for example, 95% identical to a reference sequence described herein (e.g., an antibody or antigen-binding fragment thereof described herein), the parameters are set, of course, such that the percentage of identity is calculated over the full length of the reference polypeptide sequence and that gaps in homology of up to 5% of the total number of amino acids in the reference sequence are allowed.

In some embodiments, the light chain is a kappa immunoglobulin light chain (e.g., a human kappa immunoglobulin light chain). In particular embodiments, the light chain is a kappa light chain having an allotype selected from Km1; Km1, 2; or Km3. Each of these allotypes is characterized by the following amino acid residues at the indicated positions within the IgG1 light chain (EU numbering):

Km1: V153, L191;

Km1, 2: A153, L191; and

Km3: A153, V191.

In particular embodiments, light chain is an IgG1 kappa light chain comprising one of the following amino acid sequences:

```
Km1:
                                            (SEQ ID NO: 5)
RTVAAPSVFIFPPSDEQLKSGTASVVCLLNNFYPREAKVQWKVDNVLQ
SGNSQESVTEQDSKDSTYSLSSTLTLSKADYEKHKLYACEVTHQGLSSP
VTKSFNRGEC;

Km1, 2:
                                            (SEQ ID NO: 6)
RTVAAPSVFIFPPSDEQLKSGTASVVCLLNNFYPREAKVQWKVDNALQ
SGNSQESVTEQDSKDSTYSLSSTLTLSKADYEKHKLYACEVTHQGLSSP
VTKSFNRGEC;
or

Km3:
                                            (SEQ ID NO: 7)
RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSS
PVTKSFNRGEC.
```

In some embodiments, the light chain is an IgG1 kappa light chain comprising an amino acid sequence having at least 80%, at least 85%, at least 90%, at least 95%, or at least 97% identity to any one of SEQ ID NOs:5-7.

In some embodiments, the immunoglobulin light chain or megalin-binding fragment thereof comprises an immunoglobulin light chain constant region and an immunoglobulin light chain variable region. In some embodiments, the immunoglobulin light chain or megalin-binding fragment thereof does not comprise an immunoglobulin light chain variable region.

In some embodiments, the drug-containing polymeric nanoparticles described herein are spherical. In some embodiments, the diameter of a drug-containing polymeric nanoparticle described herein is less than 90 nm. In some embodiments, the diameter of a drug-containing polymeric nanoparticle described herein is less than 80 nm. In some embodiments, the diameter of a drug-containing polymeric nanoparticle described herein is less than 60 nm. In some embodiments, the diameter of a drug-containing polymeric nanoparticle described herein is less than 50 nm. In some embodiments, the diameter of a drug-containing polymeric nanoparticle described herein is less than 25 nm. In some embodiments, the diameter of a drug-containing polymeric nanoparticle described herein is less than 10 nm. In some embodiments, the diameter of a drug-containing polymeric nanoparticle described herein is about 5 nm, about 10 nm, about 20 nm, about 30 nm, about 40 nm, about 50 nm, about 60 nm, about 70 nm, about 80 nm, about 90 nm, or about 100 nm. In some embodiments, the size of a drug-containing polymeric nanoparticle described herein is 2 nm to 100 nm, 2 to 90 nm, 2 to 80 nm, 2 to 70 nm, 2 to 60 nm, 2 to 50 nm, 2 to 25 nm, 2 to 10 nm, or 2 to 5 nm. In some embodiments, the diameter of a drug-containing polymeric nanoparticle described herein is 2 to 80 nm. In some embodiments, the diameter of a drug-containing polymeric nanoparticle described herein is 2 to 60 nm. In some embodiments, the diameter of a drug-containing polymeric nanoparticle described herein is 2 to 10 nm. In some embodiments, the diameter of a drug-containing polymeric nanoparticle described herein is 10 to 80 nm. In some embodiments, the diameter of a drug-containing polymeric nanoparticle described herein is 10 to 60 nm. In some embodiments, the diameter of a drug-containing polymeric nanoparticle described herein is 10. In some embodiments, the diameter of a drug-containing polymeric nanoparticle described herein is 60 nm. In some embodiments, the diameter of a drug-containing polymeric nanoparticle described herein is 80 nm. In some embodiments, the drug-containing polymeric nanoparticles have an overall diameter in the 2-80 nm range and are particularly useful for delivery to kidney cells (e.g., proximal tubule epithelial cells). When describing the diameter of the drug-containing polymeric nanoparticle, it is to be understood that the diameter is the diameter of the particle when conjugated to the one or more immunoglobulin light chains or megalin-binding fragments thereof.

In some embodiments, the drug-containing polymeric nanoparticles described herein are relatively neutral. In some embodiments, the zeta potential of the drug-containing polymeric particles described herein is between −10 mV and +10 mV. In some embodiments, the zeta potential of the drug-containing polymeric particles described herein is between −10 mV and 0 mV. In some embodiments, the zeta potential of the drug-containing polymeric particles described herein is between 0 mV and +10 mV. In some embodiments, the zeta potential of the drug-containing polymeric particles described herein is about −5 mV. Methods of determining the zeta potential of a nanoparticle described herein are known in the art and described in the examples below.

Methods of Conjugation

The drug-containing polymeric nanoparticles described herein are attached to (e.g., covalently conjugated) an immunoglobulin light chain or megalin-binding fragment thereof.

The immunoglobulin light chain or megalin-binding fragment thereof can be linked to the drug-containing polymeric nanoparticles through covalent attachment, e.g., through a chemical bond between a functional group on the molecule and a functional group on the drug-containing polymeric nanoparticles. A functional group can be an amino or carboxyl or other reactive groups that can be used to attach desired moieties to the nanoparticles, e.g., an immunoglobulin light chain or megalin-binding fragment thereof.

In some embodiments, the immunoglobulin light chain or megalin-binding fragment thereof can be attached to the drug-containing polymeric nanoparticles via a linker or binding agent. The linker or binding agent can have terminal amino, carboxy, sulfhydryl, or phosphate groups. Illustrative examples of useful linkers or binding agents include organic polymers, e.g., polyethylene glycol (PEG) and derivatives thereof, proteins, and small molecules.

In some embodiments, the immunoglobulin light chains or megalin-binding fragments thereof are conjugated to the drug-containing polymeric nanoparticles via covalent conjugation of maleimide groups on the surface of the polymeric nanoparticles to sulfydryl groups on the immunoglobulin light chains or megalin-binding fragments thereof. In some embodiments, the immunoglobulin light chains or megalin-binding fragments thereof are conjugated to the drug-containing polymeric nanoparticles via covalent conjugation of maleimide-PEG-amine groups on the surface of the polymeric nanoparticles to sulfydryl groups on the immunoglobulin light chains or megalin-binding fragments thereof.

In some embodiments, the immunoglobulin light chains or megalin-binding fragments thereof are conjugated to the drug-containing polymeric nanoparticles via a linker. In some embodiments, the linker comprises or consists of PEG.

Methods of Use

As described above, the present disclosure is based, at least in part, on the development of drug-containing polymeric nanoparticles that bind to megalin on kidney cells and can specifically deliver drugs (e.g., immunosuppressive or immunoregulatory drugs) to kidney tissues (e.g., proximal tubule epithelial cells in the kidney and renal cell carcinoma cells) (see Example 1 below). Drug-containing polymeric nanoparticles of the present disclosure remained in the kidneys for at least 7 days following a single injection, highlighting the retention of the payload at its intended site of action long after its administration (see Example 1 below). Accordingly, the present disclosure provides compositions and methods for treating, or delaying progression of kidney disease in a subject (e.g., a human). The compositions are useful in treating kidney diseases in which megalin-expressing cells play a role in the disease, and/or wherein the disease expresses megalin by delivering drugs to these megalin-expressing cells (e.g., proximal tubule epithelial cells and renal carcinoma cells). These methods can include identifying a subject in need of treatment and administering to the subject one or more of the compositions described herein. A subject in need of treatment can be identified, e.g., by a medical practitioner.

Provided herein is a method of treating a kidney disease in a subject, comprising administering to the subject a drug-containing polymeric particle described herein. In some embodiments, the kidney disease is kidney cancer (e.g., renal cell carcinoma). In some embodiments, the kidney disease is renal cell carcinoma. Renal cell carcinoma is the most common type of kidney cancer in adults and accounts for 90-95% of neoplasms arising from the kidney. Many cases of renal cell carcinoma are symptomless until the condition is advanced. When symptoms do occur, they include flank pain, blood in the urine, or a lump in the abdomen. Treatment of renal cell carcinoma includes removing the entire kidney or its affected part or destroying the tumor using anti-cancer therapies (e.g., radiation). If the renal cell carcinoma has metastasized, immunotherapy or localized radiation therapy may be used. In some embodiments, the kidney disease is crescentic glomerulonephritis. Crescentic glomerulonephritis (GN) is a rapidly progressive inflammatory condition affecting the kidneys, which can lead to renal failure in humans within days. Crescentic GN is defined by the light microscopic appearance of "crescents" derived from an agglomeration of visceral and parietal epithelial cells of Bowman's capsule, macrophages, T cells, renal progenitor cells, and interstitial fibroblasts in the glomeruli of the affected kidney. The formation of these crescents results in accelerated glomerulosclerosis, followed by the spread of inflammation to the tubules and interstitium of the kidney. If left untreated, the majority of patients with crescentic glomerulonephritis will die or become dialysis-dependent within six months. The spectrum of glomerular diseases associated with crescentic glomerulonephritis includes anti-glomerular basement membrane (GBM) disease, anti-neutrophil cytoplasmic antibody (ANCA)-associated vasculitis, and immune complex glomerulonephritis. In some embodiments, the kidney disease is anti-glomerular basement membrane (GBM) disease. In some embodiments, the kidney disease is anti-neutrophil cytoplasmic antibody (ANCA)-associated vasculitis. In some embodiments, the kidney disease is immune complex glomerulonephritis. In some embodiments, the kidney disease is a genetic disorder of the kidney, such as, e.g., polycystic kidney disease or a congenital transporter disease. In some embodiments, the drug-containing polymeric particle is delivered to proximal tubule epithelial cells in the subject. In some embodiments, the drug-containing polymeric particle is delivered to renal cell carcinoma cells in the subject. In some embodiments, the subject is a human.

Also provided herein is a method of delaying progression of a kidney disease in a subject, comprising administering to the subject a drug-containing polymeric particle described herein. In some embodiments, the drug-containing polymeric particle is delivered to proximal tubule epithelial cells in the subject. In some embodiments, the drug-containing polymeric particle is delivered to renal cell carcinoma cells in the subject. In some embodiments, the subject is a human. In some embodiments, the subject has a kidney disease. In some embodiments, the subject has a kidney cancer. In some embodiments, the subject has renal cell carcinoma. In some embodiments, the subject has crescentic glomerulonephritis. In some embodiments, the subject has anti-glomerular basement membrane (GBM) disease. In some embodiments, the subject has anti-neutrophil cytoplasmic antibody (ANCA)-associated vasculitis. In some embodiments, the subject has immune complex glomerulonephritis. In some embodiments, the subject has a genetic disorder of the kidney. In some embodiments, the genetic disorder of the kidney is polycystic kidney disease. In some embodiments, the genetic disorder of the kidney is a congenital transporter disease.

Also provided herein is a method of delivering one or more drugs to a kidney of a subject, the method comprising: administering a drug-containing polymeric particle described herein to the subject. In some embodiments, the drug-containing polymeric particle is delivered to proximal tubule epithelial cells in the subject. In some embodiments, the drug-containing polymeric particle is delivered to renal cell carcinoma cells in the subject. In some embodiments, the subject is a human. In some embodiments, the subject has a kidney disease. In some embodiments, the subject has a kidney cancer. In some embodiments, the subject has renal cell carcinoma. In some embodiments, the subject has crescentic glomerulonephritis. In some embodiments, the subject has anti-glomerular basement membrane (GBM) disease. In some embodiments, the subject has anti-neutrophil cytoplasmic antibody (ANCA)-associated vasculitis. In some embodiments, the subject has immune complex glomerulonephritis. In some embodiments, the subject has a genetic disorder of the kidney. In some embodiments, the genetic disorder of the kidney is polycystic kidney disease. In some embodiments, the genetic disorder of the kidney is a congenital transporter disease.

Also provided herein is a method of delivering one or more drugs to a kidney of a subject, the method comprising: administering a drug-containing polymeric particle described herein to the subject. In some embodiments, the drug-containing polymeric particle is delivered to proximal tubule epithelial cells in the subject. In some embodiments, the drug-containing polymeric particle is delivered to renal cell carcinoma cells in the subject. In some embodiments, the subject is a human. In some embodiments, the subject has a kidney disease. In some embodiments, the subject has a kidney cancer. In some embodiments, the subject has renal cell carcinoma. In some embodiments, the subject has crescentic glomerulonephritis. In some embodiments, the subject has anti-glomerular basement membrane (GBM) disease. In some embodiments, the subject has anti-neutrophil cytoplasmic antibody (ANCA)-associated vasculitis. In some embodiments, the subject has immune complex glomerulonephritis. In some embodiments, the subject has a genetic disorder of the kidney. In some embodiments, the genetic disorder of the kidney is polycystic kidney disease. In some embodiments, the genetic disorder of the kidney is a congenital transporter disease.

Also provided herein is a method of treating kidney injury in a subject, the method comprising: administering a drug-containing polymeric particle described herein to the subject. In some embodiments, the drug-containing polymeric particle is delivered to proximal tubule epithelial cells in the subject. In some embodiments, the drug-containing polymeric particle is delivered to renal cell carcinoma cells in the subject. In some embodiments, the subject is a human. In some embodiments, the kidney injury is damage to the proximal tubule. In some embodiments, the kidney injury is ischemia-reperfusion injury. In some embodiments, the kidney injury is and toxicity from antibiotics.

Also provided herein is a method of identifying renal cell carcinoma cells in a subject, comprising administering to the subject a drug-containing polymeric particle described herein to the subject, wherein the drug is a contrast agent or a dye. In some embodiments, the method further comprises determining the presence and location of the drug-containing polymeric particle in the subject.

Pharmaceutical Formulations

A therapeutically effective amount of one or more of the drug-containing polymeric nanoparticles described herein can be incorporated into pharmaceutical compositions suitable for administration to a subject, e.g., a human. Such compositions typically include the drug-containing polymeric particle and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions, e.g., an inhibitor of degradation of the ligand.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (polyethoxylated castor oil; BASF, Parsippany, NJ) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the drug-containing polymeric particle in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™ (sodium carboxymethyl starch), or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the drug-containing polymeric nanoparticles are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration. In one aspect, the pharmaceutical compositions can be included as a part of a kit.

Generally the dosage used to administer a pharmaceutical composition facilitates an intended purpose for prophylaxis and/or treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., Chapter 27 In: "Remington's Pharmaceutical Sciences", 18th Ed., Gennaro, ed., Mack Publishing Co., Easton, Pa., 1990). Generally, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., Chapter 3, In: Goodman & Gilman's "The Pharmacological Basis of Therapeutics", 9th Ed., Hardman et al., eds., McGraw-Hill, New York, N.Y., 1996).

Administration

A therapeutically effective amount of one or more of the drug-containing polymeric nanoparticles described herein can be administered to a subject (e.g., a human) by standard methods, for example, by one or more routes of administration, e.g., by one or more of the routes of administration currently approved by the United States Food and Drug Administration (FDA; see, for example world wide web address fda.gov/cder/dsm/DRG/drg00301.htm), e.g., orally, topically, mucosally, or parenterally, e.g., intravenously or intramuscularly. In some embodiments, a therapeutically effective amount of one or more of the drug-containing polymeric nanoparticles is administered to a subject (e.g., a human) via intravenous administration.

Kits

The present invention also includes kits for use in a method described herein. In some embodiments the kits comprise one or more doses of a drug-containing polymeric particle (or composition thereof) described herein. The composition, shape, and type of dosage form for the induction regimen and maintenance regimen may vary depending on a subject's requirements. For example, dosage form may be a parenteral dosage form, an oral dosage form, a delayed or controlled release dosage form, a topical, and a mucosal dosage form, including any combination thereof.

In a particular embodiment, a kit can contain one or more of the following in a package or container: (1) one or more doses of a composition described herein; (2) one or more pharmaceutically acceptable adjuvants or excipients (e.g., a pharmaceutically acceptable salt, solvate, hydrate, stereoisomer, or clathrate); (3) one or more vehicles for administration of the dose; (4) instructions for administration. Embodiments in which two or more, including all, of the components (1)-(4), are found in the same container can also be used.

When a kit is supplied, the different components of the compositions included can be packaged in separate containers and admixed immediately before use. Such packaging of the components separately can permit long term storage without loosing the active components' functions. When more than one bioactive agent is included in a particular kit, the bioactive agents may be (1) packaged separately and admixed separately with appropriate (similar of different, but compatible) adjuvants or excipients immediately before use, (2) packaged together and admixed together immediately before use, or (3) packaged separately and admixed together immediately before use. If the chosen compounds will remain stable after admixing, the compounds may be admixed at a time before use other than immediately before use, including, for example, minutes, hours, days, months, years, and at the time of manufacture.

The compositions included in particular kits of the present invention can be supplied in containers of any sort such that the life of the different components are optimally preserved and are not adsorbed or altered by the materials of the container. Suitable materials for these containers may include, for example, glass, organic polymers (e.g., polycarbonate and polystyrene), ceramic, metal (e.g., aluminum), an alloy, or any other material typically employed to hold similar reagents. Exemplary containers can include, without limitation, test tubes, vials, flasks, bottles, syringes, and the like.

As stated above, the kits can also be supplied with instructional materials. These instructions may be printed and/or may be supplied, without limitation, as an electronic-readable medium, such as a floppy disc, a CD-ROM, a DVD, a Zip disc, a video cassette, an audiotape, and a flash memory device. Alternatively, instructions may be published on an internet web site or may be distributed to the user as an electronic mail.

EXAMPLES

The invention is further described in the following examples, which do not limit the scope of the invention described in the claims.

Materials and Methods

The following materials and methods were used in the Examples set forth herein.

Nanoparticle Synthesis

A nanoprecipitation method was used to formulate fluorescent PEGylated-PLGA NPs. Briefly, 5 mg mPEG-PLGA ((Methoxy Poly(ethylene glycol)-b-Poly(D,L-lactide-co-glycolide), Mw: 5,000:30,000 Da, 50:50 LA:GA (w:w)) copolymer (AK102; Polyscitech, USA) and 1 mg PLGA-PEG-Mal ((Poly(lactide-co-glycolide)-b-poly(ethylene glycol)-maleimide, Mw: 30,000-5,000 Da, 50:50 LA:GA (w:w)) copolymer (All 10; Polyscitech) were dissolved in acetone (Sigma Aldrich, USA). Then, IRDye 800CW Carboxylate (LI-COR, USA) (IR800) was added to the polymer solution. The resultant solution was added dropwise into a 0.015% polyvinyl alcohol aqueous solution (PVA, Mw~31,000, Sigma Aldrich) under vigorous stirring for several hours at room temperature to fully evaporate organic solvent. Then, the NPs were concentrated and washed by centrifugation at 3,500 rpm, using Amicon Ultra-15 centrifugal filter units (MWCO 10 kDa, Merck Millipore Ltd, Ireland).

For microparticle synthesis, the polymers were dissolved in acetone and then IRDye 800CW Carboxylate was dispersed in the polymeric solution. The dispersed phase was emulsified in 10 mL of the aqueous phase containing 0.5% PVA using a homogenizer for several minutes. The resulting solution was added to 30 mL of deionized water containing 0.015% PVA and stirred for two hours. Vivaspin 20 Centrifugal Ultra Filter (PES Membrane, 100K MWCO) was used for the washing and concentration of the microparticles.

Surface modification of particles was achieved using a covalent linking between maleimide groups on the surface of the microparticles and sulfhydryl groups on LC proteins (Sigma-Aldrich, Cat. No. L0665). Tris(2-carboxyethyl) phosphine hydrochloride solution (TCEP, Sigma-Aldrich, USA) was used to reduce the LC proteins prior to the conjugation.

The size distribution and zeta potential of particles were determined using a Malvern Zetasizer Nano ZS system. Measurements were made in triplicates at room temperature. The morphology of NPs was visualized by transmission electron microscopy (TEM, JEOL 1200EX). Prior to imaging, the freshly prepared NPs were deposited on 200-mesh Formvar/carbon-coated copper grids and negatively stained with 0.75% uranyl acetate solution for 1 min and then washed with MilliQ water.

In Vitro Biocompatibility Evaluation

HK-2 human kidney proximal tubular epithelial cells (PTECs, CRL-2190, adult male donor, American Type Culture Collection) were cultured in RPMI 1640 (GIBCO, USA) supplemented with 10% Fetal Bovine Serum (GIBCO) and 100 μg/mL penicillin-streptomycin. Cells were incubated at 37° C. in a humidified atmosphere containing 5% C02.

To assess the toxicity of LC-NP or NP on the HK-2 cells by flow cytometry, the cells were seeded in each well of a 6-well plate ($3\times10^5$ cells/well), then 100 μl of LC-NP or NP were added to each well (total volume 1 ml) and incubated for 2, 6, and 24 hours. After incubation, the cells were washed with DPBS three times and harvested following digestion by Trypsin-EDTA (0.05%), phenol red (Thermo Fisher Scientific). Then, the cells were incubated with Fixable Viability Dye eFluor® 780 (Thermo Fisher Scientific) diluted 1:1000 in DPBS for 30 min at 4° C. Then, the cells were washed with FACS buffer (DPBS+2% fetal bovine serum+1 mM EDTA+0.1% sodium azide), prior to performance of flow cytometry using a FACSCanto™ JJ flow cytometer (BD Biosciences), and the data was analyzed using FlowJo software (FlowJo LLC, Ashland, OR).

In Vitro Binding Assay

To assess internalization of LC-NP and NP, HK-2 cells (3×105 cells) were seeded in each well of a 6-well plate and incubated overnight. Then, 100 μl of LC-NP or NP labeled with Alexa Fluor® 488 Dye (Thermo Fisher Scientific) were added to each well (total volume 1 ml) and incubated for 1 hour. After washing the cells with DPBS three times, the cells were digested and harvested. The cells were stained with Fixable Viability Dye eFluor™ 780 (Thermo Fisher Scientific) diluted 1:1000 in DPBS for 30 min at 4° C. Then, the cells were placed in FACS buffer and analyzed by flow cytometry.

To qualitatively measure the cellular uptake of LC-NP, HK-2 cells were seeded on 6-well chamber slides (ThermoFisher Scientific) at a density of 5000 cells per well. The cells were incubated with fluorescently labeled LC-NP, NP, or DPBS for 1 hour at 37° C. Then, the cells were washed three times with DPBS and fixed in acetone. The cells were stained with Anti-Lrp2/Megalin antibody (Rabbit polyclonal, Abcam) as well as mounting medium with DAPI (VECTASHIELD, Vector Laboratories Burlingame). Samples were subsequently visualized using an Evos' FL Auto 2 by Invitrogen (ThermoFisher Scientific) fluorescence microscope.

In Vivo Biodistribution Studies

Animal studies were approved and conducted according to the Institutional Animal Care and Use Committee of Brigham and Women's Hospital, Boston, MA. For tissue biodistribution studies, C57BL/6 (JAX #000664, male and female, 7-8 weeks) or BALB/c (JAX #000651, male, 7-8 weeks) mice were anesthetized with isoflurane and received a single intravenous injection of either LC-NP or unconjugated NP at the same particle concentration. 1, 2, 7, and 28 days following injection, the mice were euthanized and perfused with DPBS, and their major organs were harvested and imaged by using a UVP iBOX Explorer Imaging Microscope (UVP) equipped with a 750-780 nm excitation filter and an 800 nm long-pass emission filter. Mean fluorescence intensity (MFI) for each organ was calculated by ImageJ (National Institutes of Health; Bethesda, MD) with constant brightness values for each.

Biodistribution Studies in Tumor-Bearing Mice 100,000 Renca (ATCC® CRL-2947™) cells were implanted inside the capsule of the kidneys of BALB/c mice. Three weeks post-implantation, the mice were anesthetized via inhalation of isoflurane/oxygen, and LC-NP or NP was administered intravenously. 1, 2, and 3 days post-injection, the mice were euthanized and perfused with DPBS, and their major organs were harvested for imaging, as previously described.

Cilastatin Treatment

Female C57BL/6 mice were divided into two groups. The first group (n=4) was treated subcutaneously with 100 mg/kg Cilastatin sodium salt (>98%, Sigma Aldrich, USA) once daily for 4 days, and the second group (n=3) was treated subcutaneously with DPBS for 4 days. On the day of the last treatment, the LC-NP was injected to the mice. 1 day post injection the mice were euthanized and perfused with DPBS, and the kidneys were harvested and imaged.

Histology and Immunofluorescence Imaging

Following UVP iBOX Explorer Imaging, the kidneys and tumors were immediately frozen and embedded in optimum cutting temperature (OCT) compound (Tissue Tek, Sakura Finetek, Torrance, CA, USA). The frozen kidneys were cut into 8-μm sections with a cryomicrotome. Then, the sections were fixed in cold acetone for 10 min at room temperature, followed by immersion in 3% Bovine serum albumin (BSA, Sigma Aldrich) blocking solution. The sections were incubated overnight at 4° C. with primary antibodies, including anti-CD31 Antibody (colon MEC13.3, Biolegend), anti-Lrp2/megalin antibody (Rabbit polyclonal, abcam), anti-podoplanin antibody (Polyclonal Goat IgG, R&D Systems) and fluorescein-labeled Lotus tetragonolobus lectin (LTL, Vector Laboratories), followed by incubation with secondary antibodies (AlexaFluor® 488 goat anti-rabbit IgG, AlexaFluor® 488 goat anti-rat IgG, and AlexaFluor® 594 Rabbit anti-Goat IgG, all from ThermoFisher Scientific) for 30 min at room temperature. Slides were washed for 5 min, stained with 4,6-diamidino-2-phenylindole (DAPI), and coverslipped for fluorescence microscopy imaging.

For hematoxylin and eosin (H&E) staining, tissues were fixed in 10% formalin solution and embedded in paraffin blocks. Sections were cut and stained with H&E by conventional techniques.

Long- and Short-Term Safety of LC-NP

To study renal toxicity, the mice received a single intravenous injection of either LC-NP or NP at the same particle concentration. Separately, 4 mice were injected with vehicle (DPBS) 1, 7, and 28 days following injection, the blood was collected, and the blood urea nitrogen (BUN) was measured by the Infinity Urea kit (Thermo Fisher Scientific) and compared against a standard BUN solution of 100 mg/dL (Sigma-Aldrich) using a VersaMax microplate reader (Molecular Devices Corp., Sunnyvale, CA), as per the protocol provided by Thermo Fisher Scientific. For studying the long-term renal safety of LC-NP, 5 mice underwent intravenous administration of LC-NP weekly for one month, and their BUNs were measured by the method mentioned above.

Statistics

A two-tailed Student's t-test or one-way ANOVA was used to determine statistical significance between two groups and several groups, respectively, by using GraphPad Prism 5.0. Data represent means±SEM. *$P<0.05$; $P<0.01$; *$P<0.001$; NS: not significant.

Example 1: Selective Trafficking of a Light Chain-Conjugated Nanoparticle to the Kidney and Renal Cell Carcinoma Results Characterization of LC-NP A nanoprecipitation method was used to assemble monodispersed, spherical PEGylated NPs from mPEG-PLGA and mPEG-PLGA-Mal copolymers (FIG. 1A), prior to conjugation with reduced LCs. Reduction of the disulfide bonds between cysteine residues of LCs with TCEP, an efficient, thiol-free, and odorless agent that displays high stability within a wide range of pH[25], yielded free thiol groups, which can bind to maleimide on the surface of the NPs.

Figure 1H:
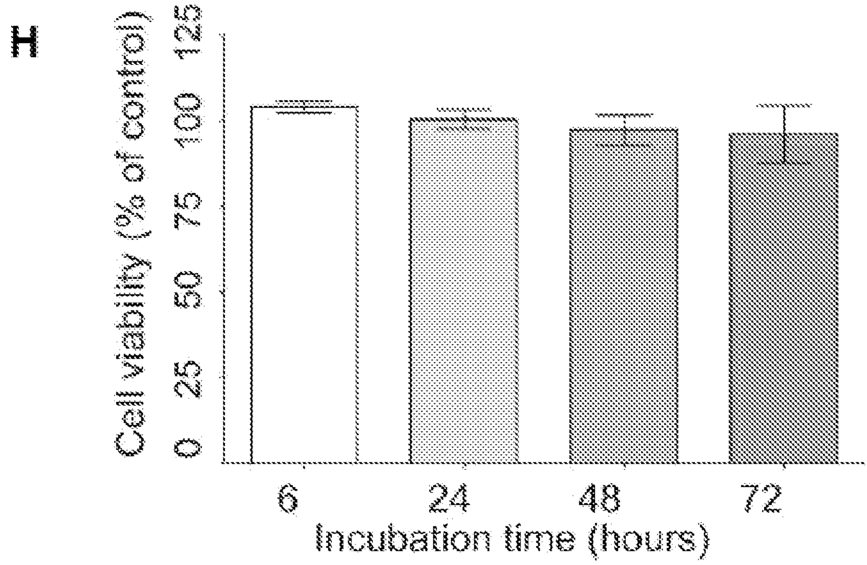
FIG. 1H-FIG. 1I.
Figure 1I:
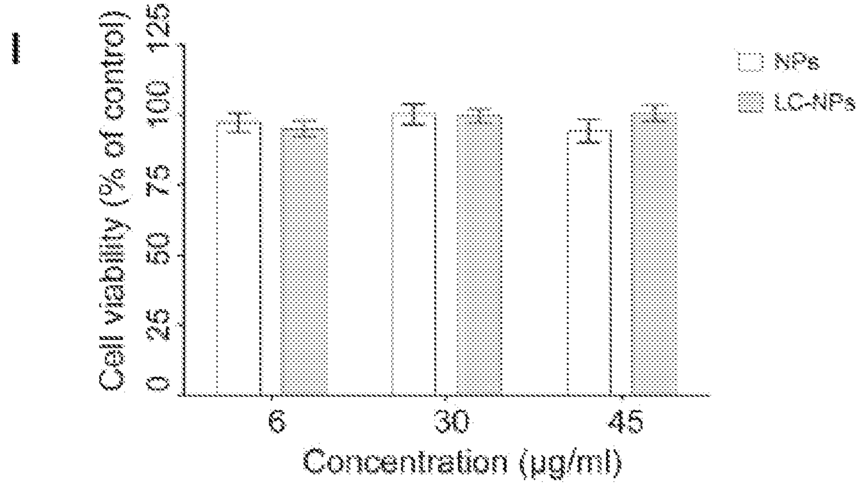
Figure 7A:
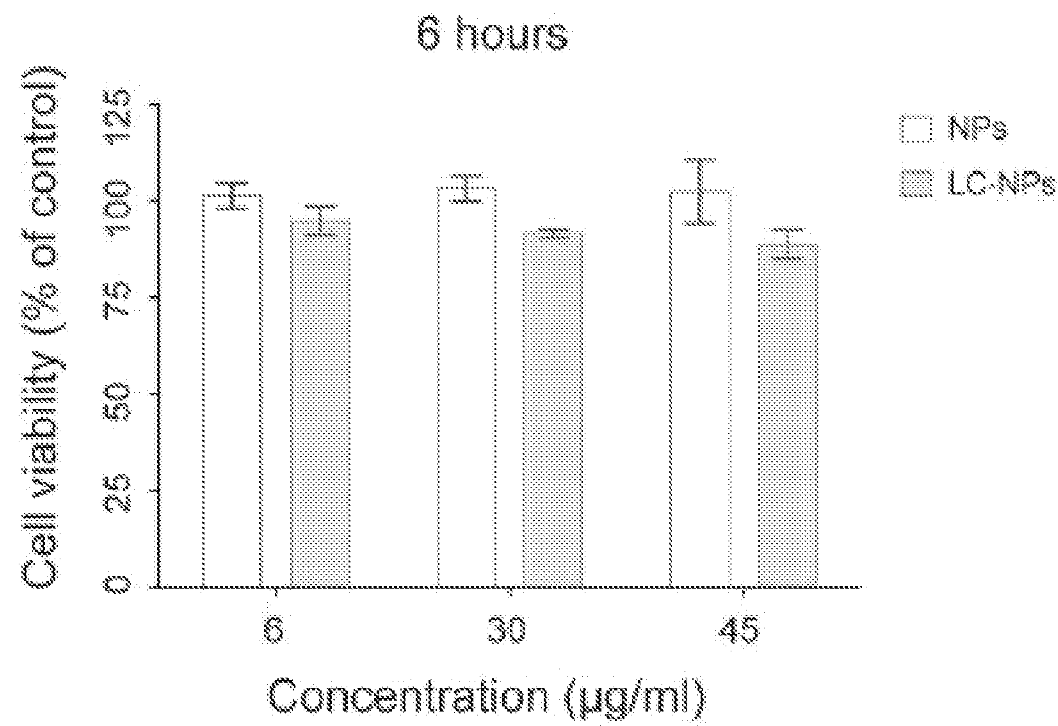
FIG. 7A-FIG. 7C. Viability of HK-2 cells with different doses of either NPs or LC-NP at (FIG. 7A) 6 hours, (FIG. 7B) 48 hours, and (FIG. 7C) 72 hours, as determined by MTT assay (n=8 replicates/condition). For each concentration, the bar on the left corresponds to NPs and the bar on the right corresponds to LC-NPs.
Figure 7B:
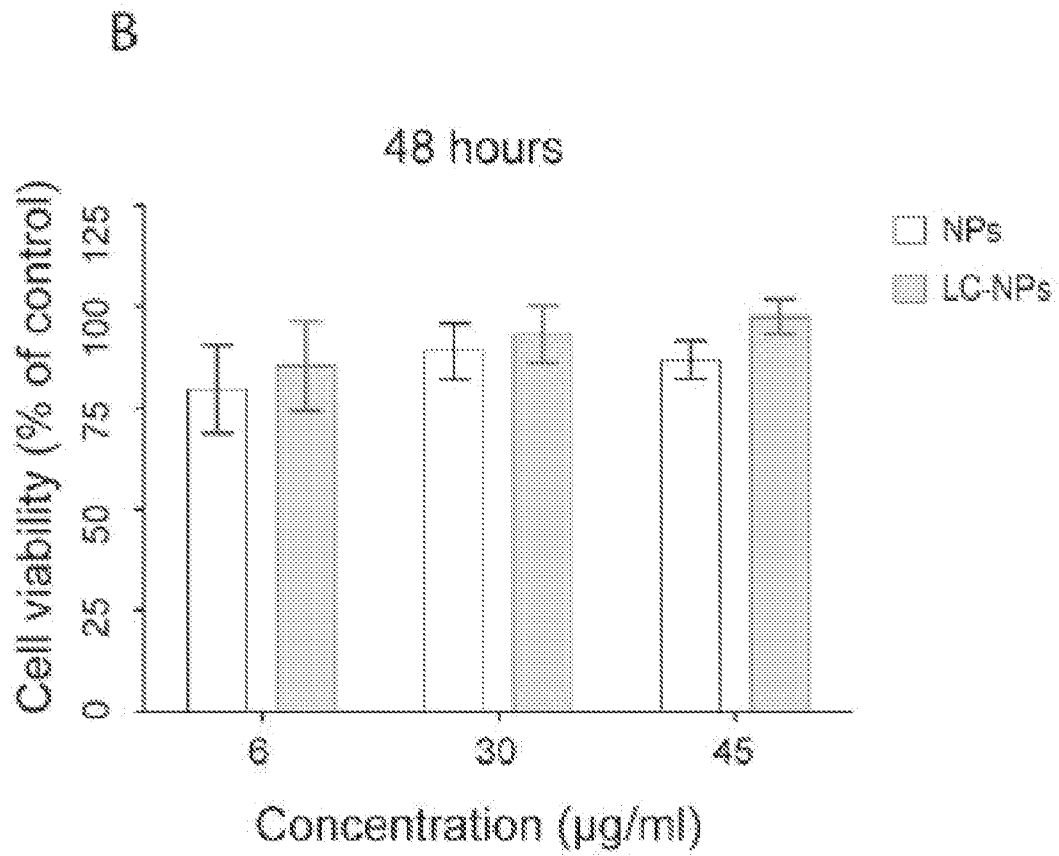
Figure 7C:
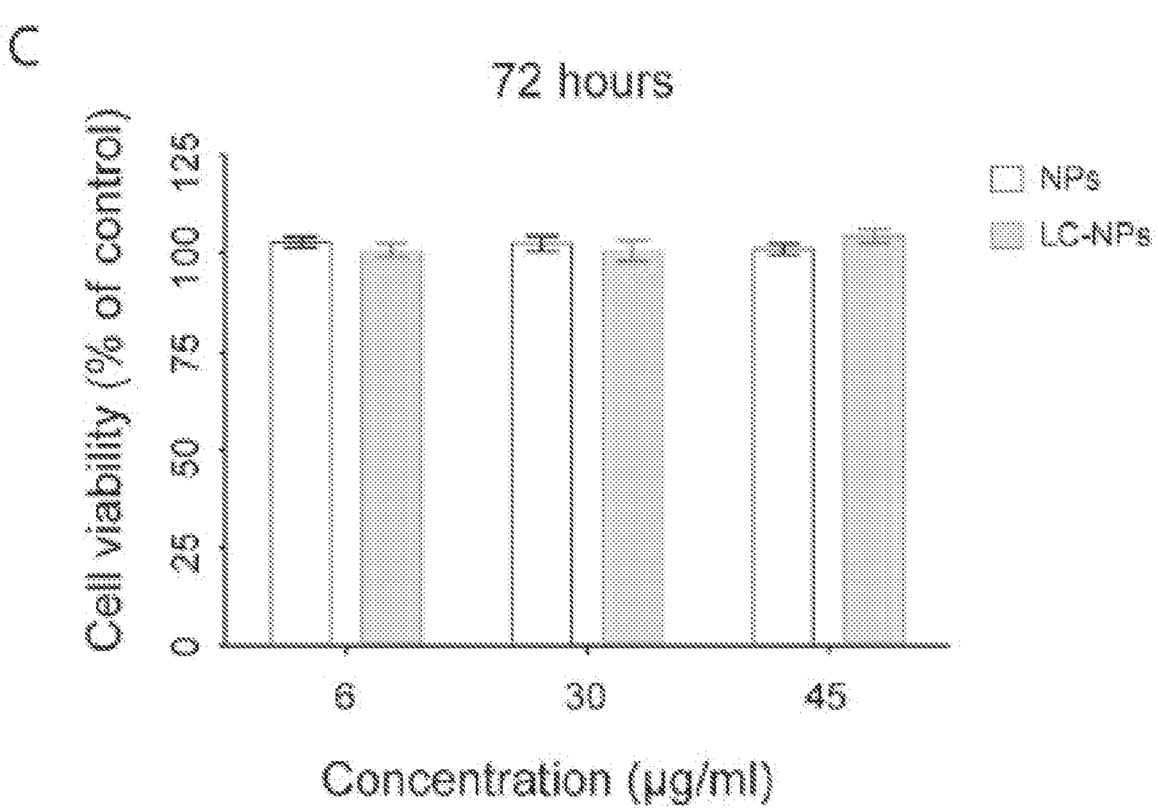

The toxicity of LC-NP to HK-2 proximal tubule epithelial cells (PTECs) was evaluated by flow cytometry over time. As shown in FIG. 1B, the viability of LC-NP-treated cells at each time point was higher than 95%, demonstrating that LC-NP was biocompatible and exerted low cellular toxicity. See also FIG. 1H, which presents additional data points relative to FIG. 1B. Moreover, over 95% of the HK-2 cells were viable following treatment with either NP or LC-NP for 24 hours, which was comparable to the control group (FIG. 1C). See also FIG. 1I, which presents additional data points relative to FIG. 1C. Similarly, no significant difference in viability was observed after 6, 48, or 72 hours or incubation with a gradient of concentrations of either NPs or LC-NPs (FIG. 7A-FIG. 7C).

Next, LC-NPs were loaded with a fluorescent dye to assess their trafficking and retention. IR800 was chosen as the fluorophore, as its emission wavelength minimizes auto-fluorescence with enhanced signal recovery and a high target-to-background contrast[26, 27]. PEG-PLGA NPs containing IR800 (NP) with an average diameter of 77.8±0.5 nm and polydispersity index (PDI) of <0.2 by dynamic light scattering (DLS) were synthesized (Table 1). IR800-NP was conjugated with LCs (LC-NP), and DLS measurements following LC conjugation displayed a slight increase in the size of LC-NP to 79.7±0.1 nm. The zeta potentials of the NP and LC-NP were −4.85±0.4 and −3.19±0.5 mV, respectively (Table 1). Without being bound by any theory, the relatively neutral (±10 mV) zeta potential of both LC-NP and NP reduces interactions with the mononuclear phagocytic system, prolongs circulation time in the systemic vasculature[28], and confers likely low repulsion by the charge-selective, negatively charged slit diaphragm between podocytes in the glomeruli of the kidney.

TABLE 1

Size and zeta potential of NPs

| | Diameter (nm) | ⁸Potential (mV) |
|---|---|---|
| NP | 77.8 ± 0.5 | −4.85 ± 0.4 |
| LC-NP | 79.7 ± 0.1 | −3.19 ± 0.5 |

To evaluate the applicability of LC-NP as a targeting vehicle for the kidney, the expression of the transmembrane protein megalin was characterized microanatomically through immunofluorescence staining, which confirmed its restriction to the proximal tubule (FIG. 1D).

Internalization of LC-NP by PTECs was confirmed by both qualitative and quantitative measures in vitro. Incubation of HK-2 PTECs with either LC-NP or NP for one hour displayed higher uptake of LC-NP by PTECs in comparison to control NP by fluorescence microscopy (FIG. 1E-FIG. 1F). Moreover, flow cytometric analysis confirmed a significantly higher presence of LC-NP in PTECs, as compared with NP (FIG. 1G).

In Vivo Targeting and Biodistribution of LC-NP

Figure 2A:
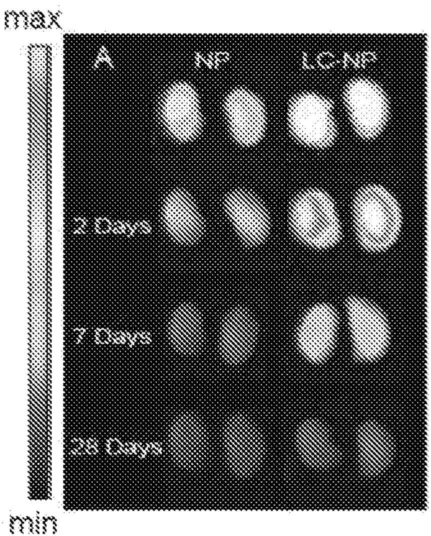
FIG. 2A-FIG. 2F. LC conjugation enhances accumulation of NP in murine kidney.
Figure 2B:
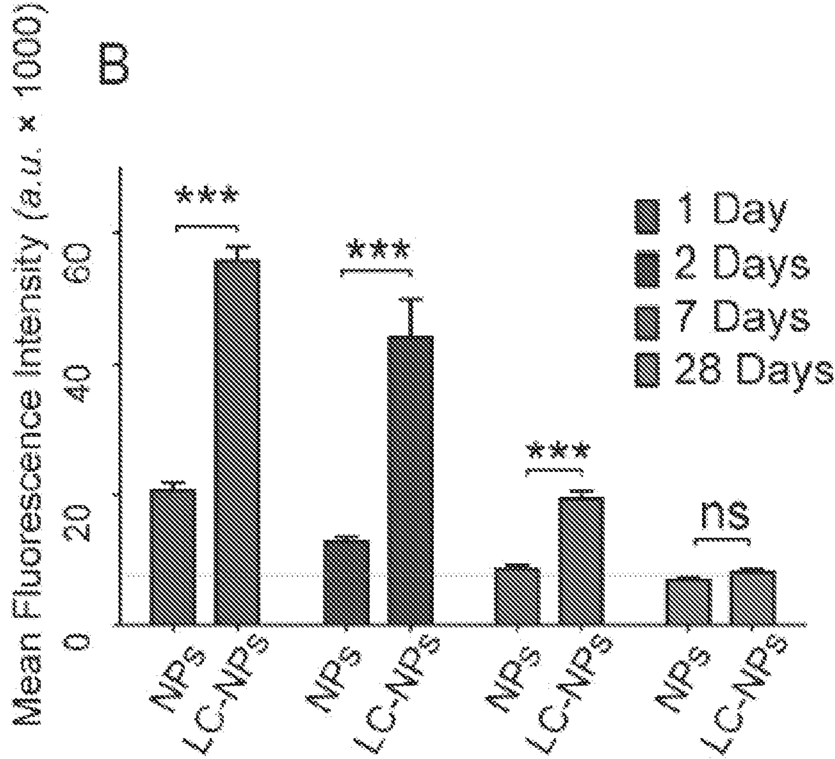
Figures 6A, 6B, 6C, 6D, 6E, 6F:
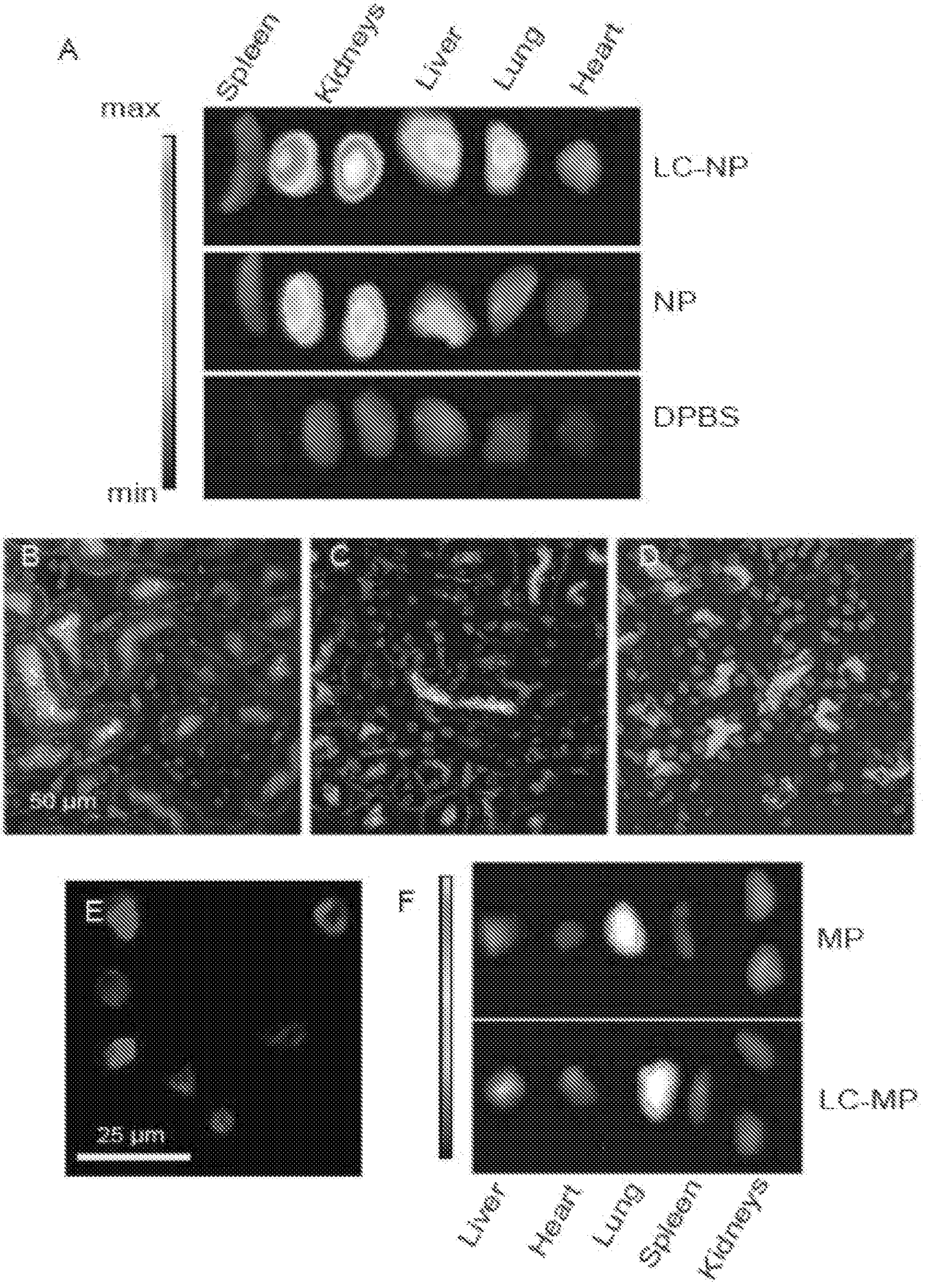
FIG. 6A-FIG. 6F.

The efficacy of LC-NP to target the kidney was studied in healthy C57BL/6 mice. Ex vivo optical imaging of murine kidneys demonstrated higher accumulation in the kidney of LC-NP-treated mice compared to the mice that received a single intravenous injection of NP (FIG. 2A). Higher mean fluorescence intensity (MFI) signal in the kidneys was observed up to 7 days following a single intravenous injection of LC-NP, as compared to the mice that received NP (2.7-fold higher at 1 day, 3.4-fold higher at 2 days, and 2.2-fold higher at 7 days post-injection) (FIG. 2B). Ex vivo organ imaging revealed that the kidneys were cleared of both LC-NP and NP at 28 days post-injection (FIG. 2A-FIG. 2B). The distribution of LC-NP to major organs was determined by fluorescence imaging. Ex vivo imaging 24 hours following intravenous injection of fluorescently labeled LC-NP revealed that most LC-NPs accumulated in the kidney, the lung and liver had the second highest signal level, and the signal was negligible in all other major organs (FIG. 6A).

Figures 2C, 2D, 2E, 2F:
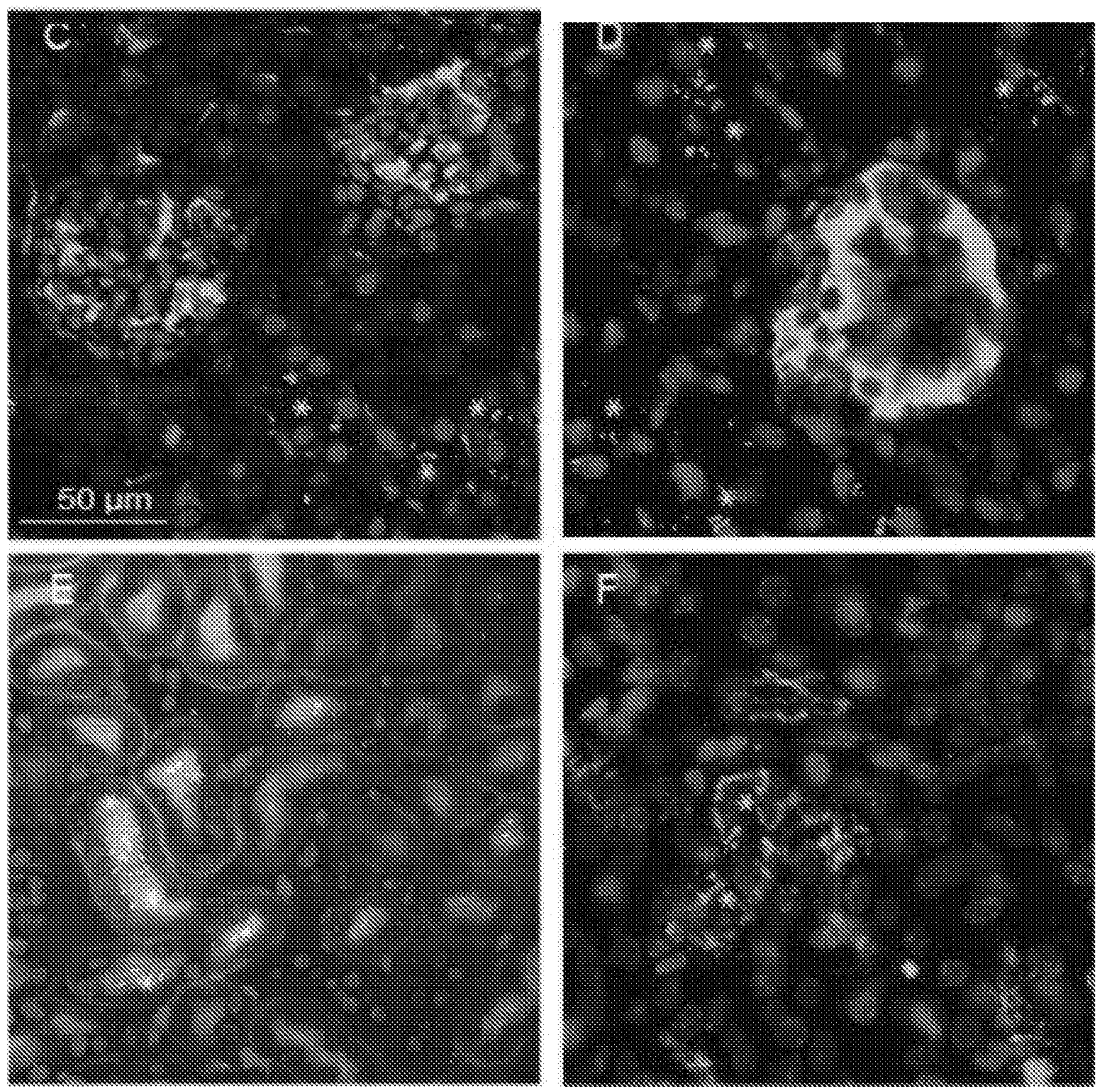

The distribution of LC-NP inside the kidney was determined by immunofluorescence staining. Localization of LC-NP was negligible in the glomeruli 24 hours following intravenous injection in C57BL/6 mice (FIG. 2C-FIG. 2D). In contrast, a large number of LC-NP localized predominantly to the apical surface of the PTECs in the kidney (FIG. 2E-FIG. 2F).

Moreover, LC-NP localized selectively and stably to the proximal tubules of the kidney for up to 7 days post-injection, as demonstrated by ex vivo imaging and immunofluorescence staining. Representative fluorescence micrographs of the kidneys at 1, 2, and 7 days following a single intravenous injection of LC-NP are shown in FIG. 6B-FIG. 6D.

Next, the mechanism by which LC-NP traffics to the PTECs in the kidney was investigated; without being bound by any particular theory, it was hypothesized that it is filtered by the glomerulus into the urinary space and tubular lumen. Therefore, the trafficking of an IR800-loaded microparticle (MP) with spherical morphology and an average size of 6.12±1.4 μm (FIG. 6E) to the kidney was studied in vivo to confirm the size restriction imparted by the fenestrated endothelium and slit diaphragm in the glomerulus to accumulation of LC-NP in the proximal tubule. As shown in FIG. 6F, MPs and LC-MPs accumulated in the lung, and no trafficking was observed to the kidney, a finding that supported our hypothesis regarding the size-selective property of localization by NPs to the proximal tubule, conferred by their requirement for glomerular filtration. Kutscher et al. reported similarly that MPs within the size range of 6-10 μm distributed mainly to the lung following intravenous injection[30].

Long- and Short-Term Safety of LC-NP

Figures 3A, 3B, 3C, 3D:
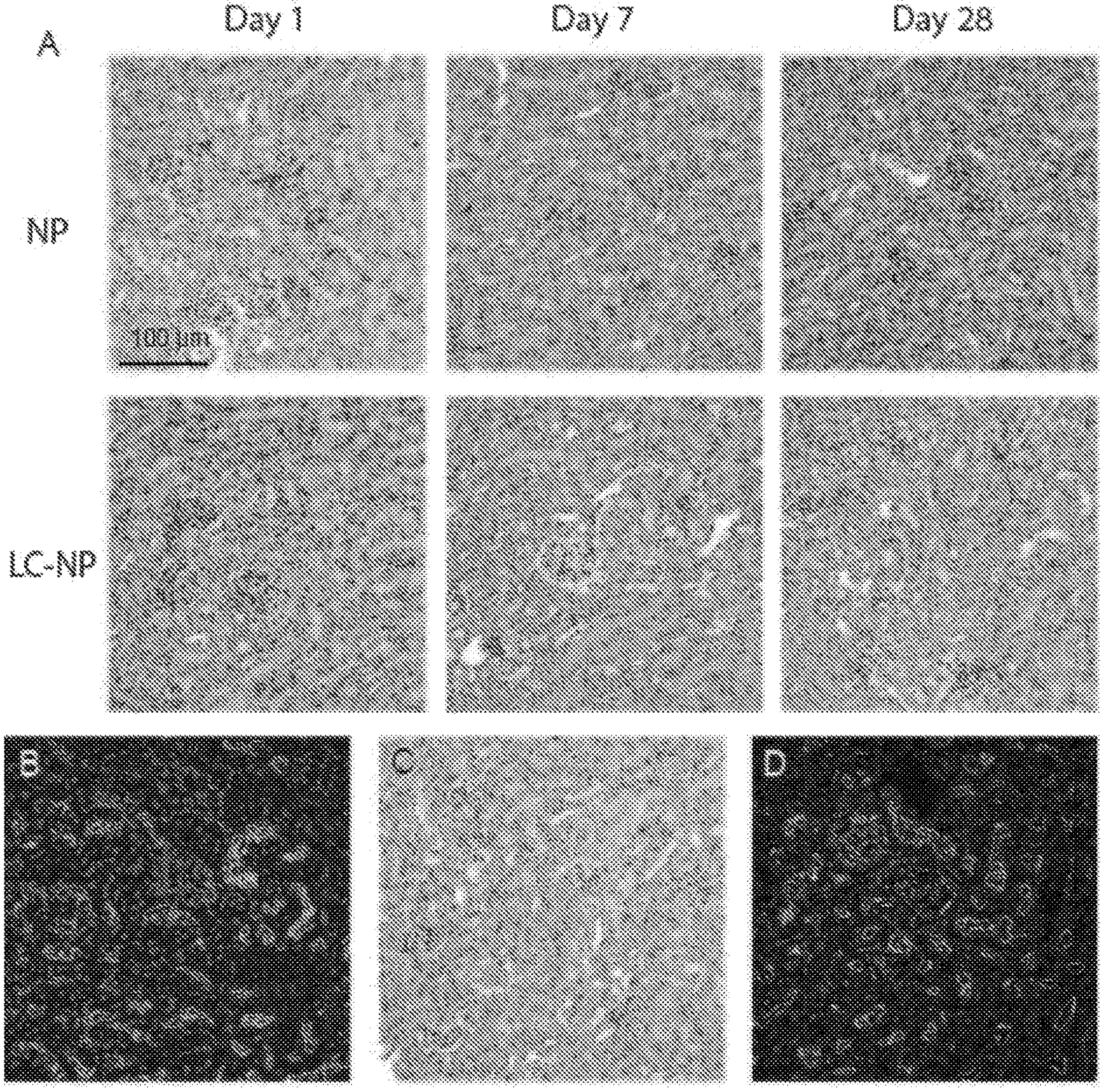
FIG. 3A-FIG. 3D.

Next, it was evaluated if the administration of LC-NP would cause damage to the kidney, as LCs can be toxic to the tubular epithelium[31, 32]. As shown in Table 2, the renal function of C57BL/6 mice injected with either LC-NP or NP, as assessed by BUN, resembled that of normal female C57BL/6 mice tested (BUN of 12-18 mg/dL), confirming the safety of LC-NP. Furthermore, histopathological evaluation of the kidney demonstrated negligible long-term changes in glomerular and proximal tubular architecture for up to 28 days post-injection (FIG. 3A). Moreover, the absence of kidney injury molecule-1 (KIM-1), an established marker of proximal tubular damage, at 7 days following injection (FIG. 3B) and the other time points (data not shown) confirmed the lack of significant toxicity.

To study the safety of repetitive treatment with LC-NP, C57BL/6 mice received intravenous injections of LC-NP weekly for up to one month. The measured BUN was comparable with the normal BUN range for C57BL/6 mice. The H&E staining of the kidney tissue revealed no change in morphology, as shown by the representative light micrographs in FIG. 3C. Furthermore, KIM-1 staining showed no sign of damage to the proximal tubules of the kidney (FIG. 3D).

TABLE 2

The renal function assessed by BUN of C57BL/6 mice injected with either NP or LC-NP.

| | BUN at Day 1 (mg/dL) | BUN at Day 7 (mg/dL) | BUN at Day 28 (mg/dL) |
|---|---|---|---|
| NP | 15.5 ± 1 | 14.5 ± 1.3 | 15.2 ± 4.15 |
| LC-NP | 15.6 ± 3.1 | 15.3 ± 1.7 | 13.9 ± 2.9 |

Megalin-Mediated Uptake of LC-NP in PTECs

Figures 4A, 4B, 4C, 4D, 4E, 4F:
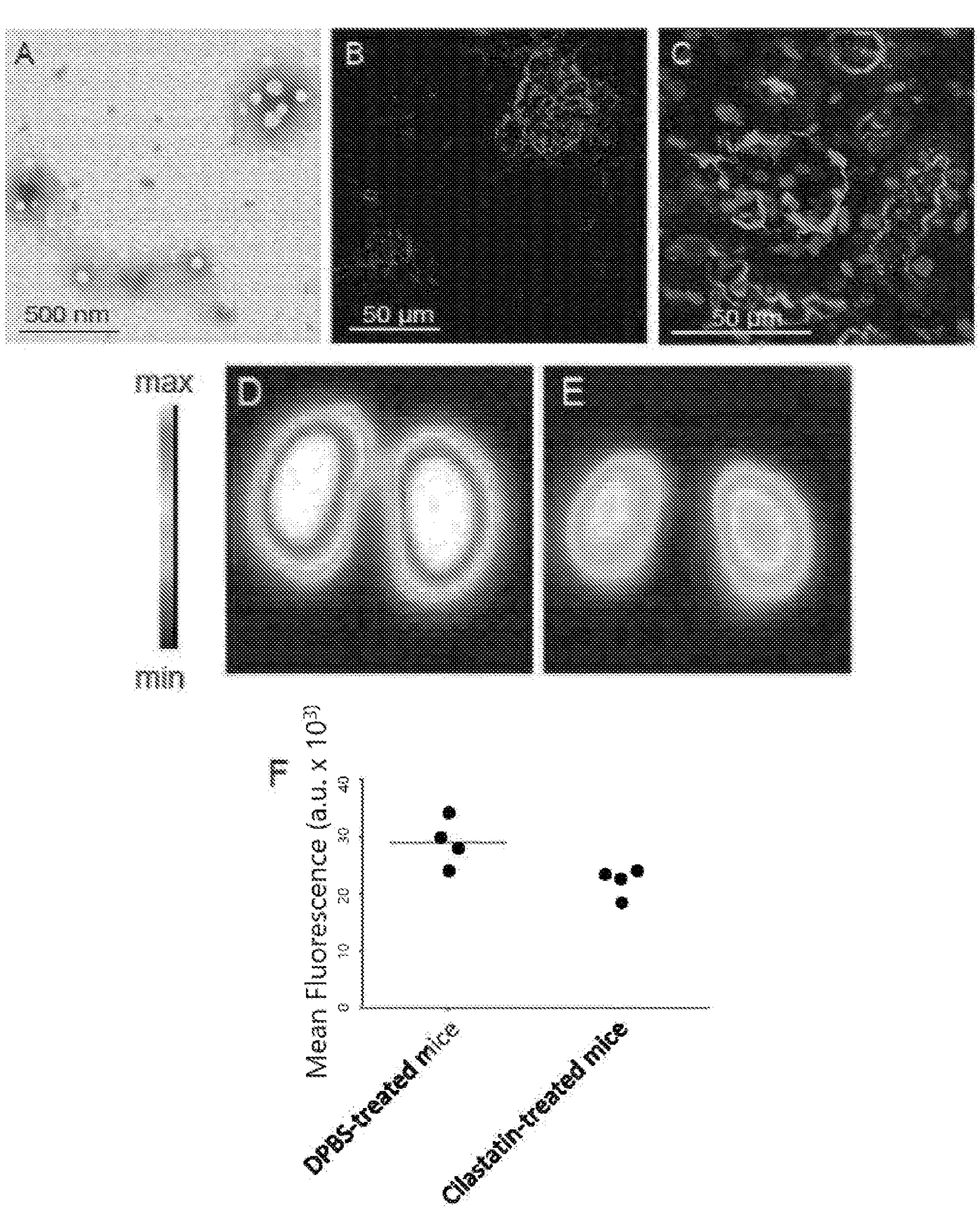
FIG. 4A-FIG. 4F. Retention of LC-NP in kidney is dependent on its binding to megalin.

Notably, observation of LC-NP in the urine immediately after injection by TEM (FIG. 4A), seen clearly in comparison to the urine of a naïve mouse (FIG. 8A), demonstrated further evidence that LC-NP undergoes swift filtration by the glomerulus (FIG. 4A). Immunofluorescence staining of the kidney tissue immediately post-injection confirmed the presence of LC-NP in the glomerulus as well as in the tubular lumen, along the apical surface of the megalin-expressing proximal tubular epithelial cells (FIG. 4B-FIG. 4C).

Figures 4G, 4H, 4I:
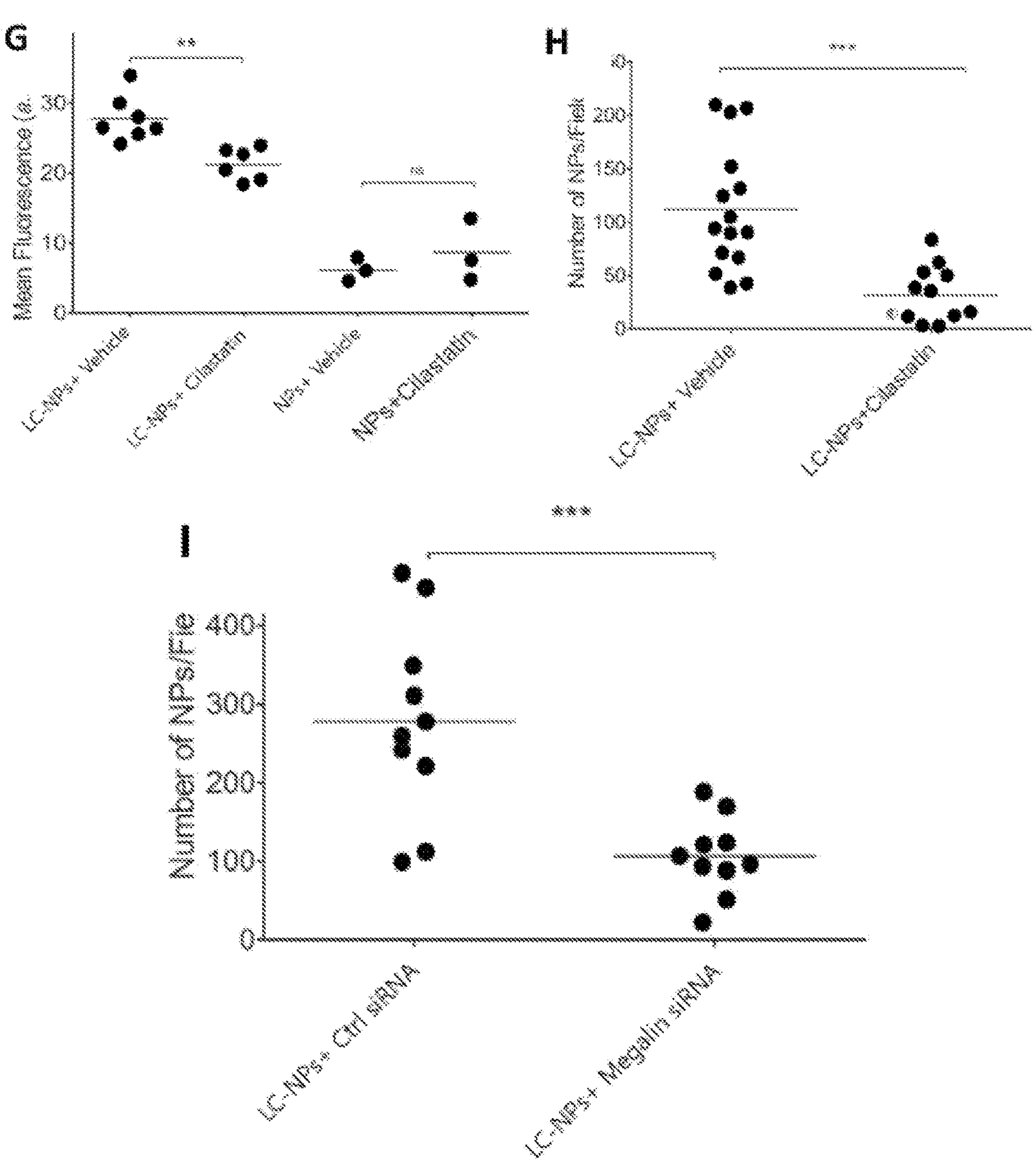
FIG. 4G-FIG. 4I.

Without being bound by any particular theory, it was hypothesized that the accumulation of LC-NP in the PTECs of the kidney is dependent on its binding to megalin. To test this hypothesis, the mice were treated with cilastatin or vehicle (DPBS) for 4 days prior to injection of LC-NP. Cilastatin, an inhibitor of renal dehydropeptidase-I (DHP-I), blocks megalin-mediated uptake in the kidney through competitive inhibition[33]. 24 hours post-injection of LC-NP, the mice were euthanized and the major organs were harvested for imaging. Representative ex vivo images of the kidneys are shown in FIG. 4D-FIG. 4E. The MFI signals from the kidneys of the mice treated with cilastatin were significantly lower than the MFI signals of the kidneys from mice treated with vehicle (FIG. 4F, FIG. 4G), indicating lower retention of LC-NP in cilastatin-treated mice in comparison to the vehicle-treated mice and confirming that the accumulation of LC-NP in the kidney was dependent on its binding to megalin. Moreover, no statistical difference was observed between vehicle and cilastatin-treated mice when the mice were injected with NPs (FIG. 4G). Next, the specific effect of cilastatin on the binding of LC-NPs to PTECs was examined by treating HK-2 human PTECs in vitro directly with LC-NPs and cilastatin. As shown in FIG. 4H, the number of LC-NPs that underwent uptake by HK-2 cells following treatment with cilastatin was significantly lower in comparison to HK-2 cells that did not receive cilastatin. Next, effective knockdown of megalin expression in HK-2 cells was performed using siRNA directed against the megalin gene. HK-2 cells treated with megalin siRNA exhibited significantly lower internalization of LC-NPs than the cells treated with the control siRNA (FIG. 4I).

In Vivo Biodistribution of LC-NP in Renal Cell Carcinoma-Bearing Mice

Figures 5A, 5B, 5C, 5D, 5E:
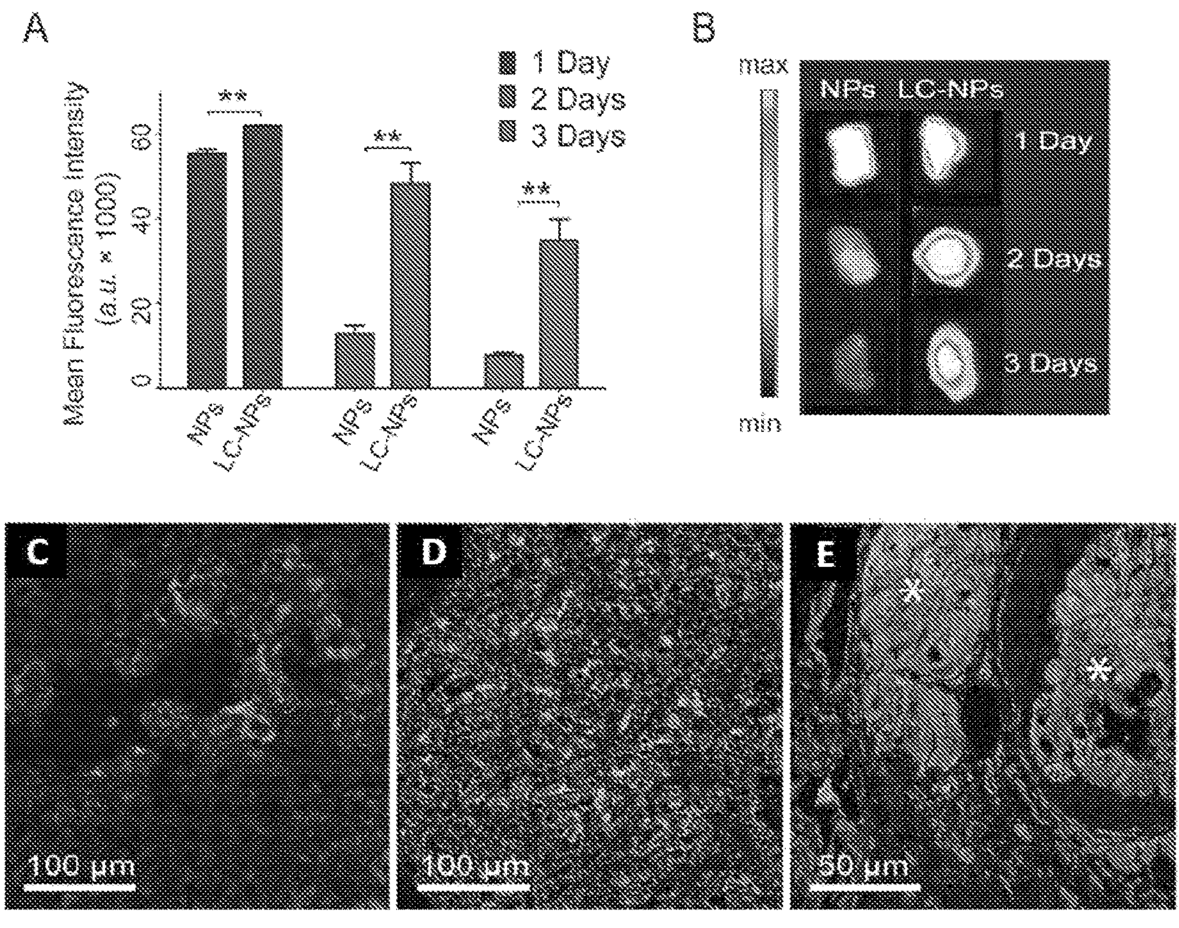
FIG. 5A-FIG. 5E. LC-NP traffics selectively to renal cell carcinoma in mice.
Figures 5F, 5G, 5H:
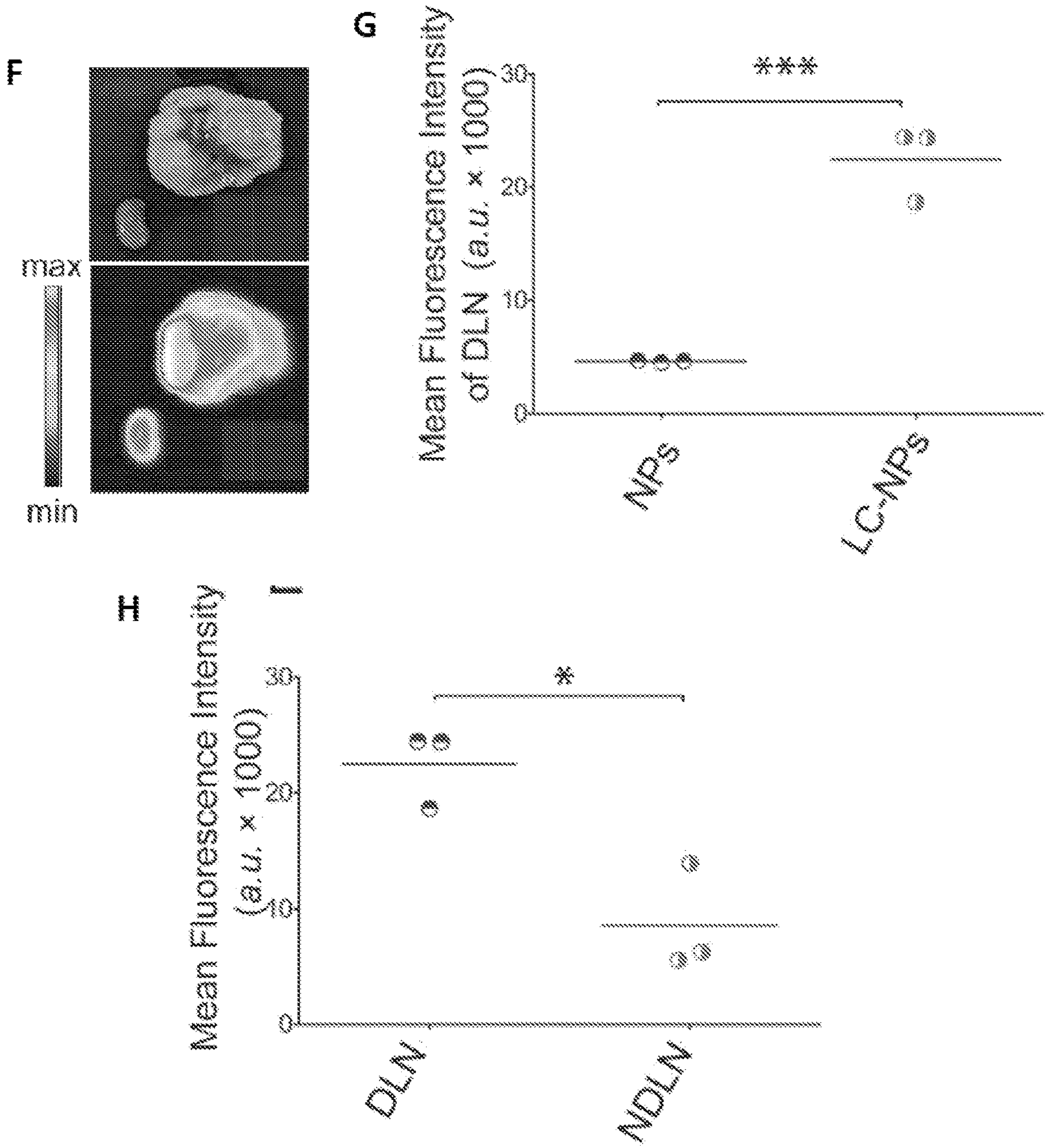
FIG. 5F-FIG. 5H.
Figures 8A, 8B, 8C, 8D:
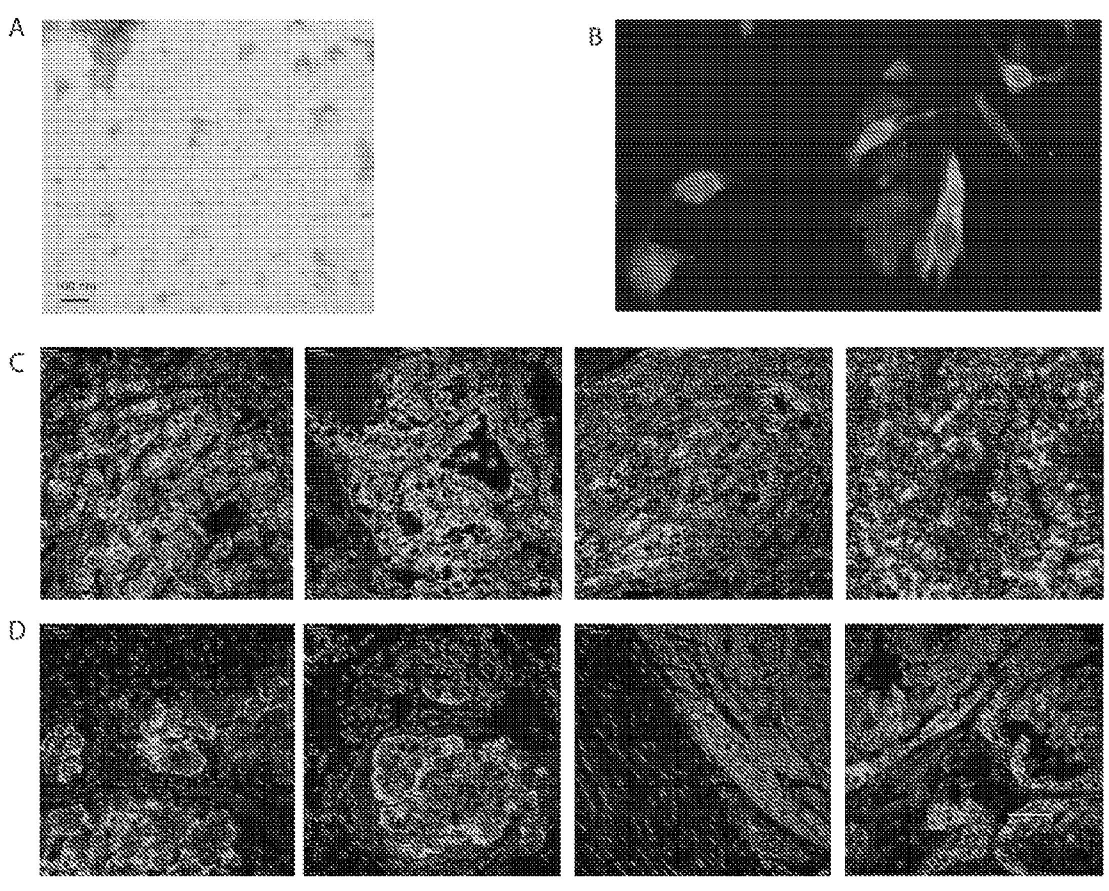
FIG. 8A-FIG. 8D.

In consideration of the selective trafficking of LC-NP to megalin-expressing PTECs, the efficacy of LC-NP to target renal cell carcinoma in murine RCC (Renca) tumor-bearing mice was evaluated. NP or LC-NP was administered intravenously to Renca tumor-bearing mice, which were then euthanized 1, 2, or 3 days following injection. Representative images of tumors from sacrificed mice at each time point are shown in FIG. 5A. Remarkably, the LC-NP-treated mice exhibited higher tumor accumulation compared to NP-treated mice at each time point (FIG. 5B). Injection of LC-NPs resulted in identification of the exophytic masses in the kidneys infiltrated by RCC, which contained a higher signal in comparison to the contralateral kidneys that were not injected with RCC, as seen in the representative photograph and ex vivo image (FIG. 5F). Then, the targeting efficacy and retention of LC-NPs in draining kidney lymph nodes (DLNs) and non-draining kidney lymph nodes (NDLNs) of RCC tumor-bearing mice was studied up to three days post-injection of a single dose of either LC-NPs or NPs. The DLNs of the mice injected with LC-NPs contained a higher signal compared to the DLNs from mice that received NPs (FIG. 5G). Moreover, the DLNs contained a higher signal compared to NDLNs, 3 days following injection of RCC tumor-bearing mice with LC-NPs (FIG. 5H). Renca tumor cells express high level of megalin as shown in FIG. 8B. Immunofluorescence staining of tumor tissue demonstrated co-localization of LC-NP with megalin-expressing cells in tumor tissue (FIG. 5C).

Finally, it was confirmed that human RCC expresses megalin very highly (FIG. 5D and FIG. 8C). Furthermore, it was found that metastatic lesions of RCC in DLN biopsies of 5 affected human patients also exhibited robust expression of megalin (FIG. 5E and FIG. 8D), demarcating these lesions clearly from the surrounding lymph node stroma.

Discussion

The field of nanomedicine constitutes a promising new frontier in nephrology research. The development of targeted drug carriers to the kidney can alter fundamentally the management of patients with renal disease, since current treatment modalities for primary renal disorders often employ drugs that exert potent off-target effects. A major unmet need for the development of kidney-targeted nanomedicine pervades the practice of clinical nephrology, as acute kidney injury affects up to 20% of all hospitalized patients worldwide[34]. However, currently no pharmacologic treatment exists for renal damage resulting from dysfunction of the proximal tubule due to ischemia-reperfusion injury, sepsis, or drug-related toxicity, which are common causes for acute kidney injury.

In this example, a light-chain conjugated PLGA NP (LC-NP) was synthesized that was designed to target the membrane protein megalin, which is expressed both by the proximal tubular epithelium in the kidney as well as renal cell carcinoma cells. LC-NP localized selectively to both of these cell types in vitro and in vivo. PLGA is a biodegradable, synthetic polymer that is FDA-approved and incorporated into several materials, including sutures, that are used widely in patient care[35]. The hydrophilic surface coating of LC-NP assists in evasion of the immune response and prolongation of systemic circulation[36].

After first establishing that the HK-2 cell proximal tubular cell line internalizes LC-NP selectively in vitro, it was confirmed that LC-NP also traffics selectively to the kidneys in vitro following injection into mice. Virtual absence of localization of LC-MP to the kidneys supports a size-selective biodistribution, and the presence of LC-NP in the glomerulus and tubular lumen shortly following injection indicates that LC-NP is likely filtered through the glomerulus into the urinary space, where it descends into the tubular lumen, prior to its internalization by PTECs. Importantly, LC-NP remained in the kidneys for at least 7 days following a single injection, reinforcing a major advantage: retention of the payload at its intended site of action, long after its administration. Without being bound by any particular theory, this property of LC-NP could reduce effectively the dosing of the agent that it delivers, an important feature that may limit the off-target toxicity of the encapsulated agent.

The specific delivery and retention of LC-NP to the proximal tubule of the kidney in comparison to other organs that contain megalin, such as lung and liver, demonstrate its applicability as a therapeutic vehicle for forms of kidney injury caused by damage to the proximal tubule, such as ischemia-reperfusion injury and toxicity from antibiotics, like aminoglycosides and possibly vancomycin.[40, 41]

Chronic exposure to toxic light chains is known to cause kidney disease through formation of casts in the tubular lumens and direct effect on the tubular epithelial cells in diseases such as multiple myeloma[43-45]. However, no significant immediate toxicity to the human proximal tubular cell line HK-2 in vitro following incubation with LC-NP was observed and no significant chronic damage to the kidneys of LC-NP-treated mice 1 month of repetitive dosing in vivo was observed.

REFERENCES

1. Farokhzad, O. C. Nanotechnology for drug delivery: the perfect partnership. Expert opinion on drug delivery 5, 927-929 (2008).
2. Farokhzad, O. C. & Langer, R. Impact of nanotechnology on drug delivery. ACS nano 3, 16-20 (2009).
3. Ferrari, M. Cancer nanotechnology: opportunities and challenges. Nature reviews. Cancer 5, 161-171 (2005).
4. Kamaly, N., Xiao, Z., Valencia, P. M., Radovic-Moreno, A. F. & Farokhzad, O. C. Targeted polymeric therapeutic nanoparticles: design, development and clinical translation. Chemical Society reviews 41, 2971-3010 (2012).
5. Shi, J., Xiao, Z., Kamaly, N. & Farokhzad, O. C. Self-assembled targeted nanoparticles: evolution of technologies and bench to bedside translation. Accounts of chemical research 44, 1123-1134 (2011).
6. Williams, R. M., Jaimes, E. A. & Heller, D. A. Nanomedicines for kidney diseases. Kidney Int 90, 740-745 (2016).
7. Williams, R. M., et al. Mesoscale Nanoparticles Selectively Target the Renal Proximal Tubule Epithelium. Nano Letters 15, 2358-2364 (2015).
8. Zuckerman, J. E. & Davis, M. E. Targeting Therapeutics to the Glomerulus With Nanoparticles. Advances in Chronic Kidney Disease 20, 500-507 (2013).
9. Zuckerman, J. E., Gale, A., Wu, P., Ma, R. & Davis, M. E. siRNA delivery to the glomerular mesangium using polycationic cyclodextrin nanoparticles containing siRNA. Nucleic Acid Ther 25, 53-64 (2015).
10. Choi, C. H. J., Zuckerman, J. E., Webster, P. & Davis, M. E. Targeting kidney mesangium by nanoparticles of defined size. Proceedings of the National Academy of Sciences 108, 6656-6661 (2011).
11. Ásgeirsdóttir, S. A., et al. Site-Specific Inhibition of Glomerulonephritis Progression by Targeted Delivery of Dexamethasone to Glomerular Endothelium. Molecular Pharmacology 72, 121-131 (2007).
12. Liang, X., et al. Short- and Long-Term Tracking of Anionic Ultrasmall Nanoparticles in Kidney. ACS Nano 10, 387-395 (2016).
13. Gao, S., et al. Megalin-mediated specific uptake of chitosan/siRNA nanoparticles in mouse kidney proximal tubule epithelial cells enables AQP1 gene silencing. Theranostics 4, 1039-1051 (2014).
14. Kim, Y. K., et al. Kidney-specific peptide-conjugated poly(ester amine) for the treatment of kidney fibrosis. Journal of nanoscience and nanotechnology 12, 5149-5154 (2012).
15. Zuckerman, J. E., Gale, A., Wu, P., Ma, R. & Davis, M. E. siRNA delivery to the glomerular mesangium using polycationic cyclodextrin nanoparticles containing siRNA. Nucleic acid therapeutics 25, 53-64 (2015).
16. Wang, J., et al. Design and in vivo characterization of kidney-targeting multimodal micelles for renal drug delivery Nano Research 11, 5584-5595 (2018).
17. Kamaly, N., He, J. C., Ausiello, D. A. & Farokhzad, O. C. Nanomedicines for renal disease: current status and future applications. Nature Reviews Nephrology 12, 738 (2016).
18. Speed, J. M., Trinh, Q. D., Choueiri, T. K. & Sun, M. Recurrence in Localized Renal Cell Carcinoma: a Systematic Review of Contemporary Data. Current urology reports 18, 15 (2017).
19. Janzen, N. K., Kim, H. L., Figlin, R. A. & Belldegrun, A. S. Surveillance after radical or partial nephrectomy for localized renal cell carcinoma and management of recurrent disease. The Urologic clinics of North America 30, 843-852 (2003).
20. Eshbach, M. L. & Weisz, O. A. Receptor-Mediated Endocytosis in the Proximal Tubule. Annu Rev Physiol 79, 425-448 (2017).
21. Verroust, P. J. & Christensen, E. I. Megalin and cubilin—the story of two multipurpose receptors unfolds. Nephrology Dialysis Transplantation 17, 1867-1871 (2002).
22. Schuetz, A. N., et al. Molecular classification of renal tumors by gene expression profiling. The Journal of molecular diagnostics: JMD 7, 206-218 (2005).
23. Saito, A., Pietromonaco, S., Loo, A. K. & Farquhar, M. G. Complete cloning and sequencing of rat gp330/"megalin," a distinctive member of the low density lipoprotein receptor gene family. Proceedings of the National Academy of Sciences 91, 9725-9729 (1994).
24. Klassen, R. B. S., Allen, P. L., Batuman, V., Crenshaw, K. & Hammond, T. G. Light chains are a ligand for megalin. Journal of Applied Physiology 98, 257-263 (2005).
25. Liu, P., et al. A Tris (2-Carboxyethyl) Phosphine (TCEP) Related Cleavage on Cysteine-Containing Proteins. Journal of the American Society for Mass Spectrometry 21, 837-844 (2010).
26. Conner, K. P., et al. Evaluation of Near Infrared Fluorescent Labeling of Monoclonal Antibodies as a Tool for Tissue Distribution. Drug Metabolism and Disposition 42, 1906-1913 (2014).
27. Meng, F., Wang, J., Ping, Q. & Yeo, Y. Quantitative Assessment of Nanoparticle Biodistribution by Fluorescence Imaging, Revisited. ACS Nano 12, 6458-6468 (2018).
28. Gustafson, H. H., Holt-Casper, D., Grainger, D. W. & Ghandehari, H. Nanoparticle Uptake: The Phagocyte Problem. Nano today 10, 487-510 (2015).
29. Sun, J., et al. Proximal Tubular Expression Patterns of Megalin and Cubilin in Proteinuric Nephropathies. Kidney international reports 2, 721-732 (2017).
30. Kutscher, H. L., et al. Threshold size for optimal passive pulmonary targeting and retention of rigid microparticles in rats. J Control Release 143, 31-37 (2010).

31. Basnayake, K., Stringer, S. J., Hutchison, C. A. & Cockwell, P. The biology of immunoglobulin free light chains and kidney injury. Kidney Int 79, 1289-1301 (2011).

32. Hutchison, C. A., et al. The pathogenesis and diagnosis of acute kidney injury in multiple myeloma. Nat Rev Nephrol 8, 43-51 (2011).

33. Hori, Y., et al. Megalin Blockade with Cilastatin Suppresses Drug-Induced Nephrotoxicity. Journal of the American Society of Nephrology 28, 1783-1791 (2017).

34. Susantitaphong, P., et al. World incidence of AKI: a meta-analysis. Clinical journal of the American Society of Nephrology: CJASN 8, 1482-1493 (2013).

35. Gentile, P., Chiono, V., Carmagnola, I. & Hatton, P. V. An overview of poly(lactic-co-glycolic) acid (PLGA)-based biomaterials for bone tissue engineering. International journal of molecular sciences 15, 3640-3659 (2014).

36. Xu, X., Ho, W., Zhang, X., Bertrand, N. & Farokhzad, O. Cancer Nanomedicine: From Targeted Delivery to Combination Therapy. Trends in molecular medicine 21, 223-232 (2015).

37. Hori, Y., et al. Megalin Blockade with Cilastatin Suppresses Drug-Induced Nephrotoxicity. Journal of the American Society of Nephrology: JASN 28, 1783-1791 (2017).

38. Eshbach, M. L. & Weisz, O. A. Receptor-Mediated Endocytosis in the Proximal Tubule. Annual review of physiology 79, 425-448 (2017).

39. Zhuang, Z., Marshansky, V., Breton, S. & Brown, D. Is caveolin involved in normal proximal tubule function? Presence in model PT systems but absence in situ. American journal of physiology. Renal physiology 300, F199-206 (2011).

40. Laurent, G., Kishore, B. K. & Tulkens, P. M. Aminoglycoside-induced renal phospholipidosis and nephrotoxicity. Biochemical pharmacology 40, 2383-2392 (1990).

41. Filippone, E. J., Kraft, W. K. & Farber, J. L. The Nephrotoxicity of Vancomycin. Clinical pharmacology and therapeutics 102, 459-469 (2017).

42. Kamaly, N., He, J. C., Ausiello, D. A. & Farokhzad, O. C. Nanomedicines for renal disease: current status and future applications. Nature reviews. Nephrology 12, 738-753 (2016).

43. Sanders, P. W. Pathogenesis and treatment of myeloma kidney. The Journal of laboratory and clinical medicine 124, 484-488 (1994).

44. Myatt, E. A., et al. Pathogenic potential of human monoclonal immunoglobulin light chains: relationship of in vitro aggregation to in vivo organ deposition. Proceedings of the National Academy of Sciences of the United States of America 91, 3034-3038 (1994).

45. Ying, W. Z., et al. Immunoglobulin light chains generate proinflammatory and profibrotic kidney injury. The Journal of clinical investigation 130, 2792-2806 (2019).

46. Motzer, R. J., et al. Kidney cancer, version 3.2015. Journal of the National Comprehensive Cancer Network: JNCCN 13, 151-159 (2015).

47. Donat, S. M., et al. Follow-up for Clinically Localized Renal Neoplasms: AUA Guideline. The Journal of urology 190, 407-416 (2013).

48. Stewart, S. B., et al. Evaluation of the National Comprehensive Cancer Network and American Urological Association renal cell carcinoma surveillance guidelines. Journal of clinical oncology: official journal of the American Society of Clinical Oncology 32, 4059-4065 (2014).

49. Adamy, A., et al. Clinical characteristics and outcomes of patients with recurrence 5 years after nephrectomy for localized renal cell carcinoma. The Journal of urology 185, 433-438 (2011).

50. Eggener, S. E., et al. Renal cell carcinoma recurrence after nephrectomy for localized disease: predicting survival from time of recurrence. Journal of clinical oncology: official journal of the American Society of Clinical Oncology 24, 3101-3106 (2006).

51. Hafez, K. S., Novick, A. C. & Campbell, S. C. Patterns of tumor recurrence and guidelines for followup after nephron sparing surgery for sporadic renal cell carcinoma. The Journal of urology 157, 2067-2070 (1997).

52. Smaldone, M. C., et al. Small renal masses progressing to metastases under active surveillance: a systematic review and pooled analysis. Cancer 118, 997-1006 (2012).

53. Shah, P. H., et al. Positive Surgical Margins Increase Risk of Recurrence after Partial Nephrectomy for High Risk Renal Tumors. The Journal of urology 196, 327-334 (2016).

54. Keefe, S. M., et al. Efficacy of the nanoparticle-drug conjugate CRLX101 in combination with bevacizumab in metastatic renal cell carcinoma: results of an investigator-initiated phase I-IIa clinical trial. Annals of oncology: official journal of the European Society for Medical Oncology 27, 1579-1585 (2016).

55. Akita, H., et al. A neutral lipid envelope-type nanoparticle composed of a pH-activated and vitamin E-scaffold lipid-like material as a platform for a gene carrier targeting renal cell carcinoma. Journal of controlled release: official journal of the Controlled Release Society 200, 97-105 (2015).

56. Chai, D., et al. Combining DNA vaccine and AIM2 in H1 nanoparticles exert anti-renal carcinoma effects via enhancing tumor-specific multi-functional CD8+ T cell responses. Molecular cancer therapeutics (2018).

57. Alsaab, H. O., et al. Tumor hypoxia directed multimodal nanotherapy for overcoming drug resistance in renal cell carcinoma and reprogramming macrophages. Biomaterials 183, 280-294 (2018).

58. Chai, D., et al. H1/pAIM2 nanoparticles exert antitumour effects that is associated with the inflammasome activation in renal carcinoma. Journal of cellular and molecular medicine 22, 5670-5681 (2018).

59. Voss, M. H., et al. A randomized phase II trial of CRLX101 in combination with bevacizumab versus standard of care in patients with advanced renal cell carcinoma. Annals of oncology. official journal of the European Society for Medical Oncology 28, 2754-2760 (2017).

60. Yang, Q., et al. Cuprous oxide nanoparticles trigger ER stress-induced apoptosis by regulating copper trafficking and overcoming resistance to sunitinib therapy in renal cancer. Biomaterials 146, 72-85 (2017).

61. Nikzad, S., et al. Effects of radiofrequency radiation in the presence of gold nanoparticles for the treatment of renal cell carcinoma. Journal of renal injury prevention 6, 103-108 (2017).

62. Yamada, Y., et al. Mitochondrial Delivery of Doxorubicin Using MITO-Porter Kills Drug-Resistant Renal Cancer Cells via Mitochondrial Toxicity. Journal of pharmaceutical sciences 106, 2428-2437 (2017).

63. Abshire, C., et al. Focused Ultrasound-Triggered Release of Tyrosine Kinase Inhibitor From Thermosensitive Liposomes for Treatment of Renal Cell Carcinoma. Journal of pharmaceutical sciences 106, 1355-1362 (2017).

64. Li, J., et al. Aptamer-Directed Specific Drug Delivery and Magnetic Resonance Imaging of Renal Carcinoma Cells In Vitro and In Vivo. Journal of biomedical nanotechnology 12, 1604-1616 (2016).

65. Liu, J., et al. Nanotechnology combined therapy: tyrosine kinase-bound gold nanorod and laser thermal ablation produce a synergistic higher treatment response of renal cell carcinoma in a murine model. BJU international 119, 342-348 (2017).

66. Callaghan, C., et al. Combined Treatment of Tyrosine Kinase Inhibitor-Labeled Gold Nanorod Encapsulated Albumin With Laser Thermal Ablation in a Renal Cell Carcinoma Model. Journal of pharmaceutical sciences 105, 284-292 (2016).

67. Liu, J., et al. Comparison of sorafenib-loaded poly (lactic/glycolic) acid and DPPC liposome nanoparticles in the in vitro treatment of renal cell carcinoma. Journal of pharmaceutical sciences 104, 1187-1196 (2015).

68. Xu, Z., et al. Comparisons of three polyethyleneimine-derived nanoparticles as a gene therapy delivery system for renal cell carcinoma. Journal of translational medicine 9, 46 (2011).

69. Yalcin, M., et al. Tetraidothyroacetic acid (tetrac) and tetrac nanoparticles inhibit growth of human renal cell carcinoma xenografts. Anticancer research 29, 3825-3831 (2009).

70. Nel, A., Ruoslahti, E. & Meng, H. New Insights into "Permeability" as in the Enhanced Permeability and Retention Effect of Cancer Nanotherapeutics. ACS nano 11, 9567-9569 (2017).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising: one or more drug-containing polymeric nanoparticles, each attached to one or more megalin-binding immunoglobulin light chains comprising any one of SEQ ID NOs: 1-7.

2. The composition of claim 1, wherein the one or more megalin-binding immunoglobulin light chains is a megalin-binding lambda immunoglobulin light chain.

3. The composition of claim 1, wherein the one or more drug-containing polymeric nanoparticles comprise an immunosuppressive or immunoregulatory drug.

4. The composition of claim 1, wherein the one or more drug-containing polymeric nanoparticles are each covalently conjugated to the one or more megalin-binding immunoglobulin light chains.

5. The composition of claim 1, wherein the one or more drug-containing polymeric nanoparticles are each attached to the one or more megalin-binding immunoglobulin light chains through a linker.

6. The composition of claim 1, further comprising a pharmaceutically acceptable carrier.

7. The composition of claim 1, wherein the one or more drug-containing polymeric nanoparticles comprises poly (lactic-co-glycolic) acid (PLGA), polylactide (PLA), or polyglycolide.

8. The composition of claim 1, further comprising polyethylene glycol.

9. A method of delivering a drug to a kidney of a subject, the method comprising:

administering the composition of claim 1 to the subject, wherein the one or more drug-containing nanopolymeric particles comprises the drug.

10. A method of delivering a drug to kidney tissue in a subject, the method comprising:

administering the composition of claim 1 to the subject, wherein the one or more drug-containing nanopolymeric particles comprises the drug.

11. A method of treating or delaying progression of a kidney disease in a subject, comprising administering to the subject the composition of claim 1.

12. The method of claim 11, wherein the kidney disease is renal cell carcinoma.

13. A method of delaying progression of a kidney disease in a subject, comprising administering to the subject the composition of claim 1.

14. The method of claim 13, wherein the kidney disease is renal cell carcinoma.

15. A method of treating kidney damage in a subject, comprising administering to the subject the composition of claim 1.

16. A method of identifying renal cell carcinoma cells in a subject, comprising administering to the subject the composition of claim 1, wherein the drug is a contrast agent or a dye.

17. The composition of claim 1, wherein the one or more megalin-binding immunoglobulin light chains is a human megalin-binding lambda immunoglobulin light chain.

18. The composition of claim 17, wherein the human megalin-binding lambda immunoglobulin light chain comprises any one of SEQ ID NOs: 1-4.

19. The composition of claim 1, wherein the one or more megalin-binding immunoglobulin light chains is a human megalin-binding kappa immunoglobulin light chain.

20. The composition of claim 19, wherein the human megalin-binding kappa immunoglobulin light chain comprises any one of SEQ ID NOs: 5-7.

* * * * *